(12) United States Patent
Lentz et al.

(10) Patent No.: US 10,076,754 B2
(45) Date of Patent: Sep. 18, 2018

(54) UNITIZED REAGENT STRIP

(71) Applicant: BECTON, DICKINSON AND COMPANY, Franklin Lakes, NJ (US)

(72) Inventors: Ammon David Lentz, York, PA (US); Richard St. Pierre, Québec (CA); Dwight Livingston, Fallston, MD (US); Adam Bruce Steel, Fallston, MD (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 15/336,429

(22) Filed: Oct. 27, 2016

(65) Prior Publication Data

US 2017/0266666 A1    Sep. 21, 2017

Related U.S. Application Data

(63) Continuation of application No. 14/974,624, filed on Dec. 18, 2015, now Pat. No. 9,480,983, which is a
(Continued)

(51) Int. Cl.
| | | |
|---|---|---|
| *G01N 35/10* | (2006.01) | |
| *B01L 3/00* | (2006.01) | |
| *B01L 9/00* | (2006.01) | |

(52) U.S. Cl.
CPC ........... *B01L 3/527* (2013.01); *B01L 3/50853* (2013.01); *G01N 35/10* (2013.01);
(Continued)

(58) Field of Classification Search
CPC .... G01N 35/10; G01N 35/00; G01N 35/1101; G01N 35/1109; B01L 3/527; B01L 3/52;
(Continued)

(56) References Cited

U.S. PATENT DOCUMENTS

| | | |
|---|---|---|
| D189,404 S | 12/1960 | Nicolle |
| 3,050,239 A | 8/1962 | Williams |

(Continued)

FOREIGN PATENT DOCUMENTS

| | | |
|---|---|---|
| CA | 2294819 | 1/1999 |
| CN | 1968754 A | 5/2007 |

(Continued)

OTHER PUBLICATIONS

Cooley et al., "Applications of Ink-Jet Printing Technology to BioMEMS and Microfluidic Systems", Proceedings, SPIE Conference on Microfluids and BioMEMS, (Oct. 2001), 12 pages.
(Continued)

*Primary Examiner* — Christine T Mui
(74) *Attorney, Agent, or Firm* — Knobbe, Martens, Olson & Bear, LLP

(57) ABSTRACT

The embodiments relate to unitized reagent strips for holding and transporting reagents and materials used in automated sample preparation and/or processing for biological and or chemical assays. In some embodiments, a first pipette sheath comprises an aperture pair. The aperture pair includes a first hole and an opposing, second hole. In some embodiments, a first pipette sheath comprises a first pipette tip aperture configured to receive a first pipette tip, and a second pipette sheath comprises a second pipette tip aperture configured to receive a second pipette tip.

20 Claims, 10 Drawing Sheets

Related U.S. Application Data continuation of application No. 14/227,883, filed on Mar. 27, 2014, now Pat. No. 9,222,954, which is a continuation of application No. PCT/US2012/058102, filed on Sep. 28, 2012.

(60) Provisional application No. 61/541,991, filed on Sep. 30, 2011.

(52) U.S. Cl.
CPC .......... *G01N 35/1011* (2013.01); *B01L 9/543* (2013.01); *B01L 2300/044* (2013.01); *B01L 2300/0609* (2013.01); *G01N 2035/103* (2013.01); *Y10T 436/119163* (2015.01)

(58) Field of Classification Search
CPC .... B01L 3/00; B01L 3/50853; B01L 3/50825; B01L 3/5082; B01L 3/50; B01L 3/508
USPC .......................... 436/54; 422/65, 400, 50, 63
See application file for complete search history.

(56) References Cited

U.S. PATENT DOCUMENTS

| | | |
|---|---|---|
| 3,905,772 A | 9/1975 | Hartnett et al. |
| 3,985,649 A | 10/1976 | Eddelman |
| 4,018,089 A | 4/1977 | Dzula et al. |
| 4,018,652 A | 4/1977 | Lanham et al. |
| 4,038,192 A | 7/1977 | Serur |
| 4,055,395 A | 10/1977 | Honkawa et al. |
| D249,706 S | 9/1978 | Adamski |
| 4,139,005 A | 2/1979 | Dickey |
| D252,157 S | 6/1979 | Kronish et al. |
| D252,341 S | 7/1979 | Thomas |
| D254,687 S | 4/1980 | Fadler et al. |
| 4,212,744 A | 7/1980 | Oota |
| D261,033 S | 9/1981 | Armbruster |
| D261,173 S | 10/1981 | Armbruster |
| 4,301,412 A | 11/1981 | Hill et al. |
| 4,439,526 A | 3/1984 | Columbus |
| 4,457,329 A | 7/1984 | Werley et al. |
| 4,466,740 A | 8/1984 | Kano et al. |
| 4,472,357 A | 9/1984 | Levy et al. |
| 4,504,582 A | 3/1985 | Swann |
| 4,522,786 A | 6/1985 | Ebersole |
| D279,817 S | 7/1985 | Chen et al. |
| D282,208 S | 1/1986 | Lowry |
| 4,599,315 A | 7/1986 | Terasaki et al. |
| 4,612,873 A | 9/1986 | Eberle |
| 4,612,959 A | 9/1986 | Costello |
| D288,478 S | 2/1987 | Carlson et al. |
| 4,647,432 A | 3/1987 | Wakatake |
| 4,654,127 A | 3/1987 | Baker et al. |
| 4,673,657 A | 6/1987 | Christian |
| 4,678,752 A | 7/1987 | Thorne et al. |
| 4,683,195 A | 7/1987 | Mullis et al. |
| 4,683,202 A | 7/1987 | Mullis |
| D292,735 S | 11/1987 | Lovborg |
| 4,720,374 A | 1/1988 | Ramachandran |
| 4,724,207 A | 2/1988 | Hou et al. |
| 4,798,693 A | 1/1989 | Mase et al. |
| 4,800,022 A | 1/1989 | Leonard |
| 4,827,944 A | 5/1989 | Nugent |
| 4,841,786 A | 6/1989 | Schulz |
| D302,294 S | 7/1989 | Hillman |
| 4,855,110 A | 8/1989 | Marker et al. |
| 4,871,779 A | 10/1989 | Killat et al. |
| 4,895,650 A | 1/1990 | Wang |
| 4,919,829 A | 4/1990 | Gates et al. |
| 4,921,809 A | 5/1990 | Schiff et al. |
| 4,935,342 A | 6/1990 | Seligson et al. |
| 4,946,562 A | 8/1990 | Guruswamy |
| 4,949,742 A | 8/1990 | Rando et al. |
| D310,413 S | 9/1990 | Bigler et al. |
| 4,963,498 A | 10/1990 | Hillman et al. |
| 4,967,950 A | 11/1990 | Legg et al. |
| D312,692 S | 12/1990 | Bradley |
| 4,978,502 A | 12/1990 | Dole et al. |
| 4,978,622 A | 12/1990 | Mishell et al. |
| 4,989,626 A | 2/1991 | Takagi et al. |
| 5,001,417 A | 3/1991 | Pumphrey et al. |
| 5,004,583 A | 4/1991 | Guruswamy et al. |
| 5,048,554 A | 9/1991 | Kremer |
| 5,053,199 A | 10/1991 | Keiser et al. |
| 5,060,823 A | 10/1991 | Perlman |
| 5,061,336 A | 10/1991 | Soane |
| 5,064,618 A | 11/1991 | Baker et al. |
| 5,071,531 A | 12/1991 | Soane |
| 5,091,328 A | 2/1992 | Miller |
| D324,426 S | 3/1992 | Fan et al. |
| 5,096,669 A | 3/1992 | Lauks et al. |
| D325,638 S | 4/1992 | Sloat et al. |
| 5,126,002 A | 6/1992 | Iwata et al. |
| 5,126,022 A | 6/1992 | Soane et al. |
| D328,135 S | 7/1992 | Fan et al. |
| D328,794 S | 8/1992 | Frenkel et al. |
| 5,135,627 A | 8/1992 | Soane |
| 5,135,872 A | 8/1992 | Pouletty et al. |
| 5,147,606 A | 9/1992 | Charlton et al. |
| 5,169,512 A | 12/1992 | Wiedenmann et al. |
| D333,522 S | 2/1993 | Gianino |
| 5,186,339 A | 2/1993 | Heissler |
| 5,192,507 A | 3/1993 | Taylor et al. |
| 5,208,163 A | 5/1993 | Charlton et al. |
| 5,217,694 A | 6/1993 | Gibler et al. |
| 5,223,226 A | 6/1993 | Wittmer et al. |
| 5,229,297 A | 7/1993 | Schnipelsky et al. |
| D338,275 S | 8/1993 | Fischer et al. |
| 5,250,263 A | 10/1993 | Manz |
| 5,252,743 A | 10/1993 | Barrett et al. |
| 5,256,376 A | 10/1993 | Callan et al. |
| 5,275,787 A | 1/1994 | Yuguchi et al. |
| 5,282,950 A | 2/1994 | Dietze et al. |
| 5,296,375 A | 3/1994 | Kricka et al. |
| 5,304,477 A | 4/1994 | Nagoh et al. |
| 5,304,487 A | 4/1994 | Wilding et al. |
| D347,478 S | 5/1994 | Pinkney |
| 5,311,896 A | 5/1994 | Kaartinen et al. |
| 5,311,996 A | 5/1994 | Duffy et al. |
| 5,316,727 A | 5/1994 | Suzuki et al. |
| 5,327,038 A | 7/1994 | Culp |
| 5,339,486 A | 8/1994 | Persic, Jr. |
| D351,475 S | 10/1994 | Gerber |
| D351,913 S | 10/1994 | Hieb et al. |
| 5,364,591 A | 11/1994 | Green et al. |
| 5,372,946 A | 12/1994 | Cusak et al. |
| 5,374,395 A | 12/1994 | Robinson |
| 5,389,339 A | 2/1995 | Petschek et al. |
| D356,232 S | 3/1995 | Armstrong et al. |
| 5,397,709 A | 3/1995 | Berndt |
| 5,401,465 A | 3/1995 | Smethers et al. |
| 5,411,708 A | 5/1995 | Moscetta et al. |
| 5,414,245 A | 5/1995 | Hackleman |
| 5,415,839 A | 5/1995 | Zaun et al. |
| 5,416,000 A | 5/1995 | Allen et al. |
| 5,422,271 A | 6/1995 | Chen et al. |
| 5,422,284 A | 6/1995 | Lau |
| 5,427,946 A | 6/1995 | Kricka et al. |
| 5,443,791 A | 8/1995 | Cathcart et al. |
| 5,474,796 A | 12/1995 | Brennan |
| D366,116 S | 1/1996 | Biskupski |
| 5,486,335 A | 1/1996 | Wilding et al. |
| 5,494,639 A | 2/1996 | Grzegorzewski |
| 5,498,392 A | 3/1996 | Wilding et al. |
| 5,503,803 A | 4/1996 | Brown |
| 5,516,410 A | 5/1996 | Schneider et al. |
| 5,519,635 A | 5/1996 | Miyake et al. |
| 5,529,677 A | 6/1996 | Schneider et al. |
| 5,559,432 A | 9/1996 | Logue |
| 5,565,171 A | 10/1996 | Dovichi et al. |
| 5,569,364 A | 10/1996 | Hooper et al. |
| 5,578,270 A | 11/1996 | Reichler et al. |
| 5,578,818 A | 11/1996 | Kain et al. |
| 5,579,928 A | 12/1996 | Anukwuem |

(56) References Cited

U.S. PATENT DOCUMENTS

| | | |
|---|---|---|
| 5,580,523 A | 12/1996 | Bard |
| 5,582,884 A | 12/1996 | Ball et al. |
| 5,582,988 A | 12/1996 | Backus et al. |
| 5,585,069 A | 12/1996 | Zanzucchi et al. |
| 5,585,089 A | 12/1996 | Queen et al. |
| 5,585,242 A | 12/1996 | Bouma et al. |
| 5,587,128 A | 12/1996 | Wilding et al. |
| 5,589,136 A | 12/1996 | Northrup et al. |
| 5,593,838 A | 1/1997 | Zanzucchi et al. |
| 5,595,708 A | 1/1997 | Berndt |
| 5,599,432 A | 2/1997 | Manz et al. |
| 5,599,503 A | 2/1997 | Manz et al. |
| 5,599,667 A | 2/1997 | Arnold, Jr. et al. |
| 5,601,727 A | 2/1997 | Bormann et al. |
| 5,603,351 A | 2/1997 | Cherukuri et al. |
| 5,605,662 A | 2/1997 | Heller et al. |
| 5,609,910 A | 3/1997 | Hackleman |
| D378,782 S | 4/1997 | LaBarbera et al. |
| 5,628,890 A | 5/1997 | Carter et al. |
| 5,630,920 A | 5/1997 | Friese et al. |
| 5,631,337 A | 5/1997 | Sassi et al. |
| 5,632,876 A | 5/1997 | Zanzucchi et al. |
| 5,632,957 A | 5/1997 | Heller et al. |
| 5,635,358 A | 6/1997 | Wilding et al. |
| 5,637,469 A | 6/1997 | Wilding et al. |
| 5,639,423 A | 6/1997 | Northrup et al. |
| 5,639,428 A | 6/1997 | Cottingham |
| 5,643,738 A | 7/1997 | Zanzucchi et al. |
| 5,645,801 A | 7/1997 | Bouma et al. |
| 5,646,039 A | 7/1997 | Northrup et al. |
| 5,646,049 A | 7/1997 | Tayi |
| 5,647,994 A | 7/1997 | Tuunanen et al. |
| 5,651,839 A | 7/1997 | Rauf |
| 5,652,141 A | 7/1997 | Henco et al. |
| 5,652,149 A | 7/1997 | Mileaf et al. |
| D382,346 S | 8/1997 | Buhler et al. |
| D382,647 S | 8/1997 | Staples et al. |
| 5,667,976 A | 9/1997 | Van Ness et al. |
| 5,671,303 A | 9/1997 | Shieh et al. |
| 5,674,394 A | 10/1997 | Whitmore |
| 5,674,742 A | 10/1997 | Northrup et al. |
| 5,681,484 A | 10/1997 | Zanzucchi et al. |
| 5,681,529 A | 10/1997 | Taguchi et al. |
| 5,683,657 A | 11/1997 | Mian |
| 5,699,157 A | 12/1997 | Parce et al. |
| 5,700,637 A | 12/1997 | Southern |
| 5,705,813 A | 1/1998 | Apffel et al. |
| 5,721,136 A | 2/1998 | Finney et al. |
| 5,725,831 A | 3/1998 | Reichler et al. |
| 5,726,026 A | 3/1998 | Wilding et al. |
| 5,726,404 A | 3/1998 | Brody |
| 5,726,944 A | 3/1998 | Pelley et al. |
| 5,731,212 A | 3/1998 | Gavin et al. |
| 5,744,366 A | 4/1998 | Kricka et al. |
| 5,746,978 A | 5/1998 | Bienhaus et al. |
| 5,747,666 A | 5/1998 | Willis |
| 5,750,015 A | 5/1998 | Soane et al. |
| 5,755,942 A | 5/1998 | Zanzucchi et al. |
| 5,762,874 A | 6/1998 | Seaton et al. |
| 5,763,262 A | 6/1998 | Wong et al. |
| 5,770,029 A | 6/1998 | Nelson et al. |
| 5,770,388 A | 6/1998 | Vorpahl |
| 5,772,966 A | 6/1998 | Maracas et al. |
| 5,779,868 A | 7/1998 | Parce et al. |
| 5,783,148 A | 7/1998 | Cottingham et al. |
| 5,787,032 A | 7/1998 | Heller et al. |
| 5,788,814 A | 8/1998 | Sun et al. |
| 5,800,600 A | 9/1998 | Lima-Marques et al. |
| 5,800,690 A | 9/1998 | Chow et al. |
| 5,804,436 A | 9/1998 | Okun et al. |
| D399,959 S | 10/1998 | Prokop et al. |
| 5,827,481 A | 10/1998 | Bente et al. |
| 5,842,106 A | 11/1998 | Thaler et al. |
| 5,842,787 A | 12/1998 | Kopf-Sill et al. |
| 5,846,396 A | 12/1998 | Zanzucchi et al. |
| 5,846,493 A | 12/1998 | Bankier et al. |
| 5,849,208 A | 12/1998 | Hayes et al. |
| 5,849,486 A | 12/1998 | Heller et al. |
| 5,849,489 A | 12/1998 | Heller |
| 5,849,598 A | 12/1998 | Wilson et al. |
| 5,852,495 A | 12/1998 | Parce |
| 5,856,174 A | 1/1999 | Lipshutz et al. |
| 5,858,187 A | 1/1999 | Ramsey et al. |
| 5,858,188 A | 1/1999 | Soane et al. |
| 5,863,502 A | 1/1999 | Southgate et al. |
| 5,863,708 A | 1/1999 | Zanzucchi et al. |
| 5,863,801 A | 1/1999 | Southgate et al. |
| 5,866,345 A | 2/1999 | Wilding et al. |
| 5,869,004 A | 2/1999 | Parce et al. |
| 5,869,244 A | 2/1999 | Martin et al. |
| 5,872,010 A | 2/1999 | Karger et al. |
| 5,872,623 A | 2/1999 | Stabile et al. |
| 5,874,046 A | 2/1999 | Megerle |
| 5,876,675 A | 3/1999 | Kennedy |
| 5,880,071 A | 3/1999 | Parce et al. |
| 5,882,465 A | 3/1999 | McReynolds |
| 5,883,211 A | 3/1999 | Sassi et al. |
| 5,885,432 A | 3/1999 | Hooper et al. |
| 5,885,470 A | 3/1999 | Parce et al. |
| 5,895,762 A | 4/1999 | Greenfield et al. |
| 5,900,130 A | 5/1999 | Benvegnu et al. |
| 5,912,124 A | 6/1999 | Kumar |
| 5,912,134 A | 6/1999 | Shartle |
| 5,914,229 A | 6/1999 | Loewy |
| 5,916,522 A | 6/1999 | Boyd et al. |
| 5,916,776 A | 6/1999 | Kumar |
| 5,919,646 A | 7/1999 | Okun et al. |
| 5,919,711 A | 7/1999 | Boyd et al. |
| 5,922,591 A | 7/1999 | Anderson et al. |
| 5,927,547 A | 7/1999 | Papen et al. |
| 5,928,880 A | 7/1999 | Wilding et al. |
| 5,929,208 A | 7/1999 | Heller et al. |
| D413,391 S | 8/1999 | Lapeus et al. |
| 5,932,799 A | 8/1999 | Moles |
| 5,935,401 A | 8/1999 | Amigo |
| 5,939,291 A | 8/1999 | Loewy et al. |
| 5,939,312 A | 8/1999 | Baier et al. |
| 5,942,443 A | 8/1999 | Parce et al. |
| D413,677 S | 9/1999 | Dumitrescu et al. |
| D414,271 S | 9/1999 | Mendoza |
| 5,948,227 A | 9/1999 | Dubrow |
| 5,948,363 A | 9/1999 | Gaillard |
| 5,948,673 A | 9/1999 | Cottingham |
| 5,955,028 A | 9/1999 | Chow |
| 5,955,029 A | 9/1999 | Wilding et al. |
| 5,957,579 A | 9/1999 | Kopf-Sill et al. |
| 5,958,203 A | 9/1999 | Parce et al. |
| 5,958,694 A | 9/1999 | Nikiforov |
| 5,959,221 A | 9/1999 | Boyd et al. |
| 5,959,291 A | 9/1999 | Jensen |
| 5,964,995 A | 10/1999 | Nikiforov et al. |
| 5,964,997 A | 10/1999 | McBride |
| 5,965,001 A | 10/1999 | Chow et al. |
| 5,965,410 A | 10/1999 | Chow et al. |
| 5,965,886 A | 10/1999 | Sauer et al. |
| 5,968,745 A | 10/1999 | Thorp et al. |
| 5,972,187 A | 10/1999 | Parce et al. |
| 5,973,138 A | 10/1999 | Collis |
| D417,009 S | 11/1999 | Boyd |
| 5,976,336 A | 11/1999 | Dubrow et al. |
| 5,980,704 A | 11/1999 | Cherukuri et al. |
| 5,980,719 A | 11/1999 | Cherukuri et al. |
| 5,981,735 A | 11/1999 | Thatcher et al. |
| 5,989,402 A | 11/1999 | Chow et al. |
| 5,992,820 A | 11/1999 | Fare et al. |
| 5,993,611 A | 11/1999 | Moroney, III et al. |
| 5,993,750 A | 11/1999 | Ghosh et al. |
| 5,997,708 A | 12/1999 | Craig |
| 6,001,229 A | 12/1999 | Ramsey |
| 6,001,231 A | 12/1999 | Kopf-Sill |
| 6,001,307 A | 12/1999 | Naka et al. |
| 6,004,515 A | 12/1999 | Parce et al. |
| 6,007,690 A | 12/1999 | Nelson et al. |
| 6,010,607 A | 1/2000 | Ramsey |

(56) References Cited

U.S. PATENT DOCUMENTS

| | | |
|---|---|---|
| 6,010,608 A | 1/2000 | Ramsey |
| 6,010,627 A | 1/2000 | Hood |
| 6,012,902 A | 1/2000 | Parce |
| D420,747 S | 2/2000 | Dumitrescu et al. |
| D421,130 S | 2/2000 | Cohen et al. |
| 6,024,920 A | 2/2000 | Cunanan |
| D421,653 S | 3/2000 | Purcell |
| 6,033,546 A | 3/2000 | Ramsey |
| 6,033,880 A | 3/2000 | Haff et al. |
| 6,043,080 A | 3/2000 | Lipshutz et al. |
| 6,046,056 A | 4/2000 | Parce et al. |
| 6,048,734 A | 4/2000 | Burns et al. |
| 6,054,034 A | 4/2000 | Soane et al. |
| 6,054,277 A | 4/2000 | Furcht et al. |
| 6,056,860 A | 5/2000 | Amigo et al. |
| 6,057,149 A | 5/2000 | Burns et al. |
| 6,062,261 A | 5/2000 | Jacobson et al. |
| 6,063,341 A | 5/2000 | Fassbind et al. |
| 6,063,589 A | 5/2000 | Kellogg et al. |
| 6,068,752 A | 5/2000 | Dubrow et al. |
| 6,071,478 A | 6/2000 | Chow |
| 6,074,725 A | 6/2000 | Kennedy |
| 6,074,827 A | 6/2000 | Nelson et al. |
| D428,497 S | 7/2000 | Lapeus et al. |
| 6,086,740 A | 7/2000 | Kennedy |
| 6,096,509 A | 8/2000 | Okun et al. |
| 6,100,541 A | 8/2000 | Nagle et al. |
| 6,102,897 A | 8/2000 | Lang |
| 6,103,537 A | 8/2000 | Ullman et al. |
| 6,106,685 A | 8/2000 | McBride et al. |
| 6,110,343 A | 8/2000 | Ramsey et al. |
| 6,117,398 A | 9/2000 | Bienhaus et al. |
| 6,123,205 A | 9/2000 | Dumitrescu et al. |
| 6,123,798 A | 9/2000 | Gandhi et al. |
| 6,130,098 A | 10/2000 | Handique et al. |
| 6,132,580 A | 10/2000 | Mathies et al. |
| 6,132,684 A | 10/2000 | Marino |
| 6,133,436 A | 10/2000 | Koster et al. |
| D433,759 S | 11/2000 | Mathis et al. |
| 6,143,250 A | 11/2000 | Tajima |
| 6,149,787 A | 11/2000 | Chow et al. |
| 6,149,872 A | 11/2000 | Mack et al. |
| 6,156,199 A | 12/2000 | Zuk |
| 6,158,269 A | 12/2000 | Dorenkott et al. |
| 6,167,910 B1 | 1/2001 | Chow |
| 6,168,948 B1 | 1/2001 | Anderson et al. |
| 6,171,850 B1 | 1/2001 | Nagle et al. |
| 6,174,675 B1 | 1/2001 | Chow et al. |
| 6,180,950 B1 | 1/2001 | Olsen |
| D438,311 S | 2/2001 | Yamanishi et al. |
| 6,190,619 B1 | 2/2001 | Kilcoin et al. |
| 6,194,563 B1 | 2/2001 | Cruickshank |
| D438,632 S | 3/2001 | Miller |
| D438,633 S | 3/2001 | Miller |
| D439,673 S | 3/2001 | Brophy et al. |
| 6,197,595 B1 | 3/2001 | Anderson et al. |
| 6,211,989 B1 | 4/2001 | Wulf et al. |
| 6,213,151 B1 | 4/2001 | Jacobson et al. |
| 6,221,600 B1 | 4/2001 | MacLeod et al. |
| 6,228,635 B1 | 5/2001 | Armstrong et al. |
| 6,232,072 B1 | 5/2001 | Fisher |
| 6,235,175 B1 | 5/2001 | Dubrow et al. |
| 6,235,313 B1 | 5/2001 | Mathiowitz et al. |
| 6,235,471 B1 | 5/2001 | Knapp et al. |
| 6,236,456 B1 | 5/2001 | Giebeler et al. |
| 6,236,581 B1 | 5/2001 | Foss et al. |
| 6,238,626 B1 | 5/2001 | Higuchi et al. |
| 6,251,343 B1 | 6/2001 | Dubrow et al. |
| 6,254,826 B1 | 7/2001 | Acosta et al. |
| 6,259,635 B1 | 7/2001 | Khouri et al. |
| 6,261,431 B1 | 7/2001 | Mathies et al. |
| 6,267,858 B1 | 7/2001 | Parce et al. |
| D446,306 S | 8/2001 | Ochi et al. |
| 6,271,021 B1 | 8/2001 | Burns et al. |
| 6,274,089 B1 | 8/2001 | Chow et al. |
| 6,280,967 B1 | 8/2001 | Ransom et al. |
| 6,281,008 B1 | 8/2001 | Komai et al. |
| 6,284,113 B1 | 9/2001 | Bjornson et al. |
| 6,284,470 B1 | 9/2001 | Bitner et al. |
| 6,287,254 B1 | 9/2001 | Dodds |
| 6,287,774 B1 | 9/2001 | Nikiforov |
| 6,291,248 B1 | 9/2001 | Haj-Ahmad |
| 6,294,063 B1 | 9/2001 | Becker et al. |
| 6,302,134 B1 | 10/2001 | Kellogg et al. |
| 6,302,304 B1 | 10/2001 | Spencer |
| 6,303,343 B1 | 10/2001 | Kopf-Sill |
| 6,306,273 B1 | 10/2001 | Wainright et al. |
| 6,306,590 B1 | 10/2001 | Mehta et al. |
| 6,310,199 B1 | 10/2001 | Smith et al. |
| 6,316,774 B1 | 11/2001 | Giebeler et al. |
| 6,319,469 B1 | 11/2001 | Mian et al. |
| 6,322,683 B1 | 11/2001 | Wolk et al. |
| 6,326,083 B1 | 12/2001 | Yang et al. |
| 6,326,147 B1 | 12/2001 | Oldham et al. |
| 6,326,211 B1 | 12/2001 | Anderson et al. |
| 6,334,980 B1 | 1/2002 | Hayes et al. |
| 6,337,435 B1 | 1/2002 | Chu et al. |
| 6,353,475 B1 | 3/2002 | Jensen et al. |
| 6,358,387 B1 | 3/2002 | Kopf-sill et al. |
| 6,366,924 B1 | 4/2002 | Parce |
| 6,368,561 B1 | 4/2002 | Rutishauser et al. |
| 6,368,871 B1 | 4/2002 | Christel et al. |
| 6,370,206 B1 | 4/2002 | Schenk |
| 6,375,185 B1 | 4/2002 | Lin |
| 6,375,901 B1 | 4/2002 | Robotti et al. |
| 6,379,884 B2 | 4/2002 | Wada et al. |
| 6,379,929 B1 | 4/2002 | Burns et al. |
| 6,379,974 B1 | 4/2002 | Parce et al. |
| 6,382,254 B1 | 5/2002 | Yang et al. |
| 6,391,541 B1 | 5/2002 | Petersen et al. |
| 6,391,623 B1 | 5/2002 | Besemer et al. |
| 6,395,161 B1 | 5/2002 | Schneider et al. |
| 6,398,956 B1 | 6/2002 | Coville et al. |
| 6,399,025 B1 | 6/2002 | Chow |
| 6,399,389 B1 | 6/2002 | Parce et al. |
| 6,399,952 B1 | 6/2002 | Maher et al. |
| 6,401,552 B1 | 6/2002 | Elkins |
| 6,403,338 B1 | 6/2002 | Knapp et al. |
| 6,408,878 B2 | 6/2002 | Unger et al. |
| 6,413,401 B1 | 7/2002 | Chow et al. |
| 6,416,642 B1 | 7/2002 | Alajoki et al. |
| 6,420,143 B1 | 7/2002 | Kopf-sill |
| 6,425,972 B1 | 7/2002 | McReynolds |
| D461,906 S | 8/2002 | Pham |
| 6,428,987 B2 | 8/2002 | Franzen |
| 6,430,512 B1 | 8/2002 | Gallagher |
| 6,432,366 B2 | 8/2002 | Ruediger et al. |
| 6,440,725 B1 | 8/2002 | Pourahmadi et al. |
| D463,031 S | 9/2002 | Slomski et al. |
| 6,444,461 B1 | 9/2002 | Knapp et al. |
| 6,447,661 B1 | 9/2002 | Chow et al. |
| 6,447,727 B1 | 9/2002 | Parce et al. |
| 6,448,064 B1 | 9/2002 | Vo-Dinh et al. |
| 6,453,928 B1 | 9/2002 | Kaplan et al. |
| 6,458,259 B1 | 10/2002 | Parce et al. |
| 6,461,570 B2 | 10/2002 | Ishihara et al. |
| 6,465,257 B1 | 10/2002 | Parce et al. |
| 6,468,761 B2 | 10/2002 | Yang et al. |
| 6,472,141 B2 | 10/2002 | Nikiforov |
| D466,219 S | 11/2002 | Wynschenk et al. |
| 6,475,364 B1 | 11/2002 | Dubrow et al. |
| D467,348 S | 12/2002 | McMichael et al. |
| D467,349 S | 12/2002 | Niedbala et al. |
| 6,488,897 B2 | 12/2002 | Dubrow et al. |
| 6,495,104 B1 | 12/2002 | Unno et al. |
| 6,498,497 B1 | 12/2002 | Chow et al. |
| 6,500,323 B1 | 12/2002 | Chow et al. |
| 6,500,390 B1 | 12/2002 | Boulton et al. |
| D468,437 S | 1/2003 | McMenamy et al. |
| 6,506,609 B1 | 1/2003 | Wada et al. |
| 6,509,193 B1 | 1/2003 | Tajima |
| 6,511,853 B1 | 1/2003 | Kopf-sill et al. |
| D470,595 S | 2/2003 | Crisanti et al. |
| 6,515,753 B2 | 2/2003 | Maher et al. |

(56) References Cited

U.S. PATENT DOCUMENTS

| | | |
|---|---|---|
| 6,517,783 B2 | 2/2003 | Horner et al. |
| 6,520,197 B2 | 2/2003 | Deshmukh et al. |
| 6,521,188 B1 | 2/2003 | Webster |
| 6,524,456 B1 | 2/2003 | Ramsey et al. |
| 6,524,790 B1 | 2/2003 | Kopf-sill et al. |
| D472,324 S | 3/2003 | Rumore et al. |
| 6,534,295 B2 | 3/2003 | Tai et al. |
| 6,537,771 B1 | 3/2003 | Farinas et al. |
| 6,540,896 B1 | 4/2003 | Manz et al. |
| 6,544,734 B1 | 4/2003 | Briscoe et al. |
| 6,547,942 B1 | 4/2003 | Parce et al. |
| 6,555,389 B1 | 4/2003 | Ullman et al. |
| 6,556,923 B2 | 4/2003 | Gallagher et al. |
| D474,279 S | 5/2003 | Mayer et al. |
| D474,280 S | 5/2003 | Niedbala et al. |
| 6,558,916 B2 | 5/2003 | Veerapandian et al. |
| 6,558,945 B1 | 5/2003 | Kao |
| 6,569,607 B2 | 5/2003 | McReynolds |
| 6,572,830 B1 | 6/2003 | Burdon et al. |
| 6,575,188 B2 | 6/2003 | Parunak |
| 6,576,459 B2 | 6/2003 | Miles et al. |
| 6,579,453 B1 | 6/2003 | Bächler et al. |
| 6,589,729 B2 | 7/2003 | Chan et al. |
| 6,592,821 B1 | 7/2003 | Wada et al. |
| 6,597,450 B1 | 7/2003 | Andrews et al. |
| 6,602,474 B1 | 8/2003 | Tajima |
| 6,613,211 B1 | 9/2003 | Mccormick et al. |
| 6,613,512 B1 | 9/2003 | Kopf-sill et al. |
| 6,613,580 B1 | 9/2003 | Chow et al. |
| 6,613,581 B1 | 9/2003 | Wada et al. |
| 6,614,030 B2 | 9/2003 | Maher et al. |
| 6,620,625 B2 | 9/2003 | Wolk et al. |
| 6,623,860 B2 | 9/2003 | Hu et al. |
| 6,627,406 B1 | 9/2003 | Singh et al. |
| D480,814 S | 10/2003 | Lafferty et al. |
| 6,632,655 B1 | 10/2003 | Mehta et al. |
| 6,633,785 B1 | 10/2003 | Kasahara et al. |
| D482,796 S | 11/2003 | Oyama et al. |
| 6,640,981 B2 | 11/2003 | Lafond et al. |
| 6,649,358 B1 | 11/2003 | Parce et al. |
| 6,664,104 B2 | 12/2003 | Pourahmadi et al. |
| 6,669,831 B2 | 12/2003 | Chow et al. |
| 6,670,153 B2 | 12/2003 | Stern |
| D484,989 S | 1/2004 | Gebrian |
| 6,672,458 B2 | 1/2004 | Hansen et al. |
| 6,681,616 B2 | 1/2004 | Spaid et al. |
| 6,681,788 B2 | 1/2004 | Parce et al. |
| 6,685,813 B2 | 2/2004 | Williams et al. |
| 6,692,700 B2 | 2/2004 | Handique |
| 6,695,009 B2 | 2/2004 | Chien et al. |
| 6,699,713 B2 | 3/2004 | Benett et al. |
| 6,706,519 B1 | 3/2004 | Kellogg et al. |
| 6,720,148 B1 | 4/2004 | Nikiforov |
| 6,730,206 B2 | 5/2004 | Ricco et al. |
| 6,733,645 B1 | 5/2004 | Chow |
| 6,734,401 B2 | 5/2004 | Bedingham et al. |
| 6,737,026 B1 | 5/2004 | Bergh et al. |
| 6,740,518 B1 | 5/2004 | Duong et al. |
| D491,272 S | 6/2004 | Alden et al. |
| D491,273 S | 6/2004 | Biegler et al. |
| D491,276 S | 6/2004 | Langille |
| 6,750,661 B2 | 6/2004 | Brooks et al. |
| 6,752,966 B1 | 6/2004 | Chazan |
| 6,756,019 B1 | 6/2004 | Dubrow et al. |
| 6,764,859 B1 | 7/2004 | Kreuwel et al. |
| 6,766,817 B2 | 7/2004 | Dias da Silva |
| 6,773,567 B1 | 8/2004 | Wolk |
| 6,777,184 B2 | 8/2004 | Nikiforov et al. |
| 6,783,962 B1 | 8/2004 | Olander et al. |
| D495,805 S | 9/2004 | Lea et al. |
| 6,787,015 B2 | 9/2004 | Lackritz et al. |
| 6,787,016 B2 | 9/2004 | Tan et al. |
| 6,787,111 B2 | 9/2004 | Roach et al. |
| 6,790,328 B2 | 9/2004 | Jacobson et al. |
| 6,790,330 B2 | 9/2004 | Gascoyne et al. |
| 6,811,668 B1 | 11/2004 | Berndt et al. |
| 6,818,113 B2 | 11/2004 | Williams et al. |
| 6,819,027 B2 | 11/2004 | Saraf |
| 6,824,663 B1 | 11/2004 | Boone |
| D499,813 S | 12/2004 | Wu |
| D500,142 S | 12/2004 | Crisanti et al. |
| D500,363 S | 12/2004 | Fanning et al. |
| 6,827,831 B1 | 12/2004 | Chow et al. |
| 6,827,906 B1 | 12/2004 | Bjornson et al. |
| 6,838,156 B1 | 1/2005 | Neyer et al. |
| 6,838,680 B2 | 1/2005 | Maher et al. |
| 6,852,287 B2 | 2/2005 | Ganesan |
| 6,858,185 B1 | 2/2005 | Kopf-sill et al. |
| 6,859,698 B2 | 2/2005 | Schmeisser |
| 6,861,035 B2 | 3/2005 | Pham et al. |
| 6,878,540 B2 | 4/2005 | Pourahmadi et al. |
| 6,878,755 B2 | 4/2005 | Singh et al. |
| 6,884,628 B2 | 4/2005 | Hubbell et al. |
| 6,887,693 B2 | 5/2005 | McMillan et al. |
| 6,893,879 B2 | 5/2005 | Petersen et al. |
| 6,900,889 B2 | 5/2005 | Bjornson et al. |
| 6,905,583 B2 | 6/2005 | Wainright et al. |
| 6,905,612 B2 | 6/2005 | Dorian et al. |
| 6,906,797 B1 | 6/2005 | Kao et al. |
| 6,908,594 B1 | 6/2005 | Schaevitz et al. |
| 6,911,183 B1 | 6/2005 | Handique et al. |
| 6,914,137 B2 | 7/2005 | Baker |
| 6,915,679 B2 | 7/2005 | Chien et al. |
| 6,918,404 B2 | 7/2005 | Dias da Silva |
| D508,999 S | 8/2005 | Fanning et al. |
| 6,939,451 B2 | 9/2005 | Zhao et al. |
| 6,942,771 B1 | 9/2005 | Kayyem |
| 6,958,392 B2 | 10/2005 | Fomovskaia et al. |
| D512,155 S | 11/2005 | Matsumoto |
| 6,964,747 B2 | 11/2005 | Banerjee et al. |
| 6,977,163 B1 | 12/2005 | Mehta |
| 6,984,516 B2 | 1/2006 | Briscoe et al. |
| D515,707 S | 2/2006 | Sinohara et al. |
| D516,221 S | 2/2006 | Wohlstadter et al. |
| 7,001,853 B1 | 2/2006 | Brown et al. |
| 7,004,184 B2 | 2/2006 | Handique et al. |
| D517,554 S | 3/2006 | Yanagisawa et al. |
| 7,010,391 B2 | 3/2006 | Handique et al. |
| 7,023,007 B2 | 4/2006 | Gallagher |
| 7,024,281 B1 | 4/2006 | Unno |
| 7,036,667 B2 | 5/2006 | Greenstein et al. |
| 7,037,416 B2 | 5/2006 | Parce et al. |
| 7,038,472 B1 | 5/2006 | Chien |
| 7,039,527 B2 | 5/2006 | Tripathi et al. |
| 7,040,144 B2 | 5/2006 | Spaid et al. |
| 7,041,258 B2 | 5/2006 | Desmond et al. |
| 7,049,558 B2 | 5/2006 | Baer et al. |
| D523,153 S | 6/2006 | Akashi et al. |
| 7,055,695 B2 | 6/2006 | Greenstein et al. |
| 7,060,171 B1 | 6/2006 | Nikiforov et al. |
| 7,066,586 B2 | 6/2006 | Dias da Silva |
| 7,069,952 B1 | 7/2006 | McReynolds et al. |
| 7,072,036 B2 | 7/2006 | Jones et al. |
| 7,099,778 B2 | 8/2006 | Chien |
| D528,215 S | 9/2006 | Malmsater |
| 7,101,467 B2 | 9/2006 | Spaid |
| 7,105,304 B1 | 9/2006 | Nikiforov et al. |
| D531,321 S | 10/2006 | Godfrey et al. |
| 7,118,910 B2 | 10/2006 | Unger et al. |
| 7,138,032 B2 | 11/2006 | Gandhi et al. |
| D534,280 S | 12/2006 | Gomm et al. |
| 7,148,043 B2 | 12/2006 | Kordunsky et al. |
| 7,150,814 B1 | 12/2006 | Parce et al. |
| 7,150,999 B1 | 12/2006 | Shuck |
| D535,403 S | 1/2007 | Isozaki et al. |
| 7,160,423 B2 | 1/2007 | Chien et al. |
| 7,161,356 B1 | 1/2007 | Chien |
| 7,169,277 B2 | 1/2007 | Ausserer et al. |
| 7,169,618 B2 | 1/2007 | Skold |
| D537,951 S | 3/2007 | Okamoto et al. |
| D538,436 S | 3/2007 | Patadia et al. |
| 7,192,557 B2 | 3/2007 | Wu et al. |
| 7,195,986 B1 | 3/2007 | Bousse et al. |
| 7,205,154 B2 | 4/2007 | Corson |

(56) References Cited

U.S. PATENT DOCUMENTS

| | | |
|---|---|---|
| 7,208,125 B1 | 4/2007 | Dong |
| 7,235,406 B1 | 6/2007 | Woudenberg et al. |
| 7,247,274 B1 | 7/2007 | Chow |
| D548,841 S | 8/2007 | Brownell et al. |
| D549,827 S | 8/2007 | Maeno et al. |
| 7,252,928 B1 | 8/2007 | Hafeman et al. |
| 7,270,786 B2 | 9/2007 | Parunak et al. |
| D554,069 S | 10/2007 | Bolotin et al. |
| D554,070 S | 10/2007 | Bolotin et al. |
| 7,276,208 B2 | 10/2007 | Sevigny et al. |
| 7,276,330 B2 | 10/2007 | Chow et al. |
| 7,288,228 B2 | 10/2007 | Lefebvre |
| D556,914 S | 12/2007 | Okamoto et al. |
| 7,303,727 B1 | 12/2007 | Dubrow et al. |
| D559,995 S | 1/2008 | Handique et al. |
| 7,323,140 B2 | 1/2008 | Handique et al. |
| 7,332,130 B2 | 2/2008 | Handique |
| 7,338,760 B2 | 3/2008 | Gong et al. |
| D566,291 S | 4/2008 | Parunak et al. |
| 7,351,377 B2 | 4/2008 | Chazan et al. |
| D569,526 S | 5/2008 | Duffy et al. |
| 7,374,949 B2 | 5/2008 | Kuriger |
| 7,390,460 B2 | 6/2008 | Osawa et al. |
| 7,419,784 B2 | 9/2008 | Dubrow et al. |
| 7,422,669 B2 | 9/2008 | Jacobson et al. |
| 7,440,684 B2 | 10/2008 | Spaid et al. |
| 7,476,313 B2 | 1/2009 | Siddiqi |
| 7,480,042 B1 | 1/2009 | Phillips et al. |
| 7,494,577 B2 | 2/2009 | Williams et al. |
| 7,494,770 B2 | 2/2009 | Wilding et al. |
| 7,514,046 B2 | 4/2009 | Kechagia et al. |
| 7,518,726 B2 | 4/2009 | Rulison et al. |
| 7,521,186 B2 | 4/2009 | Burd Mehta |
| 7,527,769 B2 | 5/2009 | Bunch et al. |
| D595,423 S | 6/2009 | Johansson et al. |
| 7,553,671 B2 | 6/2009 | Sinclair et al. |
| D596,312 S | 7/2009 | Giraud et al. |
| D598,566 S | 8/2009 | Allaer |
| D599,234 S | 9/2009 | Ito |
| 7,595,197 B2 | 9/2009 | Brasseur |
| 7,604,938 B2 | 10/2009 | Takahashi et al. |
| 7,635,588 B2 | 12/2009 | King et al. |
| 7,645,581 B2 | 1/2010 | Knapp et al. |
| 7,670,559 B2 | 3/2010 | Chien et al. |
| 7,674,431 B2 | 3/2010 | Ganesan |
| 7,689,022 B2 | 3/2010 | Weiner et al. |
| 7,704,735 B2 | 4/2010 | Facer et al. |
| 7,723,123 B1 | 5/2010 | Murphy et al. |
| D618,820 S | 6/2010 | Wilson et al. |
| 7,727,371 B2 | 6/2010 | Kennedy et al. |
| 7,727,477 B2 | 6/2010 | Boronkay et al. |
| 7,744,817 B2 | 6/2010 | Bui |
| D621,060 S | 8/2010 | Handique |
| D628,305 S | 11/2010 | Gorrec et al. |
| 7,867,776 B2 | 1/2011 | Kennedy et al. |
| D632,799 S | 2/2011 | Canner et al. |
| 7,892,819 B2 | 2/2011 | Wilding et al. |
| D637,737 S | 5/2011 | Wilson et al. |
| 7,955,864 B2 | 6/2011 | Cox et al. |
| 7,998,708 B2 | 8/2011 | Handique et al. |
| 8,071,056 B2 | 12/2011 | Burns et al. |
| 8,088,616 B2 | 1/2012 | Handique |
| 8,105,783 B2 | 1/2012 | Handique |
| 8,110,158 B2 | 2/2012 | Handique |
| 8,133,671 B2 | 3/2012 | Williams et al. |
| 8,182,763 B2 | 5/2012 | Duffy et al. |
| 8,246,919 B2 | 8/2012 | Herchenbach et al. |
| 8,273,308 B2 | 9/2012 | Handique et al. |
| D669,597 S | 10/2012 | Cavada et al. |
| 8,287,820 B2 | 10/2012 | Williams et al. |
| 8,323,584 B2 | 12/2012 | Ganesan |
| 8,323,900 B2 | 12/2012 | Handique et al. |
| 8,324,372 B2 | 12/2012 | Brahmasandra et al. |
| 8,415,103 B2 | 4/2013 | Handique |
| 8,420,015 B2 | 4/2013 | Ganesan et al. |
| 8,440,149 B2 | 5/2013 | Handique |
| 8,470,586 B2 | 6/2013 | Wu et al. |
| 8,473,104 B2 | 6/2013 | Handique et al. |
| D686,749 S | 7/2013 | Trump |
| D687,567 S | 8/2013 | Jungheim et al. |
| D692,162 S | 10/2013 | Lentz et al. |
| 8,679,831 B2 | 3/2014 | Handique et al. |
| D702,854 S | 4/2014 | Nakahana et al. |
| 8,685,341 B2 | 4/2014 | Ganesan |
| 8,703,069 B2 | 4/2014 | Handique et al. |
| 8,709,787 B2 | 4/2014 | Handique |
| 8,710,211 B2 | 4/2014 | Brahmasandra et al. |
| 8,734,733 B2 | 5/2014 | Handique |
| D710,024 S | 7/2014 | Guo |
| 8,765,076 B2 | 7/2014 | Handique et al. |
| 8,852,862 B2 | 10/2014 | Wu et al. |
| 8,883,490 B2 | 11/2014 | Handique et al. |
| 8,894,947 B2 | 11/2014 | Ganesan et al. |
| 8,895,311 B1 | 11/2014 | Handique et al. |
| D729,404 S | 5/2015 | Teich et al. |
| 9,028,773 B2 | 5/2015 | Ganesan |
| 9,040,288 B2 | 5/2015 | Handique et al. |
| 9,051,604 B2 | 6/2015 | Handique |
| 9,080,207 B2 | 7/2015 | Handique et al. |
| D742,027 S | 10/2015 | Lentz et al. |
| 9,186,677 B2 | 11/2015 | Williams et al. |
| 9,217,143 B2 | 12/2015 | Brahmasandra et al. |
| 9,222,954 B2 | 12/2015 | Lentz et al. |
| 9,238,223 B2 | 1/2016 | Handique |
| 9,259,734 B2 | 2/2016 | Williams et al. |
| 9,259,735 B2 | 2/2016 | Handique et al. |
| 9,347,586 B2 | 5/2016 | Williams et al. |
| 9,480,983 B2 | 11/2016 | Lentz et al. |
| 9,528,142 B2 | 12/2016 | Handique |
| 9,618,139 B2 | 4/2017 | Handique |
| D787,008 S | 6/2017 | Duffy et al. |
| 9,670,528 B2 | 6/2017 | Handique et al. |
| 9,677,121 B2 | 6/2017 | Ganesan et al. |
| 9,701,957 B2 | 7/2017 | Wilson et al. |
| 9,745,623 B2 | 8/2017 | Steel |
| 9,765,389 B2 | 9/2017 | Gubatayao et al. |
| 9,802,199 B2 | 10/2017 | Handique et al. |
| 9,815,057 B2 | 11/2017 | Handique |
| 2001/0005489 A1 | 6/2001 | Roach et al. |
| 2001/0012492 A1 | 8/2001 | Acosta et al. |
| 2001/0016358 A1 | 8/2001 | Osawa et al. |
| 2001/0021355 A1 | 9/2001 | Baugh et al. |
| 2001/0023848 A1 | 9/2001 | Gjerde et al. |
| 2001/0038450 A1 | 11/2001 | McCaffrey et al. |
| 2001/0045358 A1 | 11/2001 | Kopf-Sill et al. |
| 2001/0046702 A1 | 11/2001 | Schembri |
| 2001/0048899 A1 | 12/2001 | Marouiss et al. |
| 2001/0055765 A1 | 12/2001 | O'Keefe et al. |
| 2002/0001848 A1 | 1/2002 | Bedingham et al. |
| 2002/0008053 A1 | 1/2002 | Hansen et al. |
| 2002/0009015 A1 | 1/2002 | Laugharn, Jr. et al. |
| 2002/0014443 A1 | 2/2002 | Hansen et al. |
| 2002/0015667 A1 | 2/2002 | Chow |
| 2002/0021983 A1 | 2/2002 | Comte et al. |
| 2002/0022261 A1 | 2/2002 | Anderson et al. |
| 2002/0037499 A1 | 3/2002 | Quake et al. |
| 2002/0039783 A1 | 4/2002 | McMillan et al. |
| 2002/0053399 A1 | 5/2002 | Soane et al. |
| 2002/0054835 A1 | 5/2002 | Robotti et al. |
| 2002/0055167 A1 | 5/2002 | Pourahmadi et al. |
| 2002/0058332 A1 | 5/2002 | Quake et al. |
| 2002/0060156 A1 | 5/2002 | Mathies et al. |
| 2002/0068357 A1 | 6/2002 | Mathies et al. |
| 2002/0068821 A1 | 6/2002 | Gundling |
| 2002/0090320 A1 | 7/2002 | Burow et al. |
| 2002/0094303 A1 | 7/2002 | Yamamoto et al. |
| 2002/0131903 A1 | 9/2002 | Ingenhoven et al. |
| 2002/0141903 A1 | 10/2002 | Parunak et al. |
| 2002/0142471 A1 | 10/2002 | Handique et al. |
| 2002/0143297 A1 | 10/2002 | Francavilla et al. |
| 2002/0143437 A1 | 10/2002 | Handique et al. |
| 2002/0155010 A1 | 10/2002 | Karp et al. |
| 2002/0155477 A1 | 10/2002 | Ito |
| 2002/0169518 A1 | 11/2002 | Luoma et al. |

(56) References Cited

U.S. PATENT DOCUMENTS

| | | |
|---|---|---|
| 2002/0187557 A1 | 12/2002 | Hobbs et al. |
| 2002/0192808 A1 | 12/2002 | Gambini et al. |
| 2003/0008308 A1 | 1/2003 | Enzelberger et al. |
| 2003/0019522 A1 | 1/2003 | Parunak |
| 2003/0022392 A1 | 1/2003 | Hudak |
| 2003/0049174 A1 | 3/2003 | Ganesan |
| 2003/0049833 A1 | 3/2003 | Chen et al. |
| 2003/0059823 A1 | 3/2003 | Matsunaga et al. |
| 2003/0064507 A1 | 4/2003 | Gallagher et al. |
| 2003/0070677 A1 | 4/2003 | Handique et al. |
| 2003/0072683 A1 | 4/2003 | Stewart et al. |
| 2003/0073106 A1 | 4/2003 | Johansen et al. |
| 2003/0083686 A1 | 5/2003 | Freeman et al. |
| 2003/0087300 A1 | 5/2003 | Knapp et al. |
| 2003/0096310 A1 | 5/2003 | Hansen et al. |
| 2003/0099954 A1 | 5/2003 | Miltenyi et al. |
| 2003/0127327 A1 | 7/2003 | Kurnik |
| 2003/0136679 A1 | 7/2003 | Bohn et al. |
| 2003/0156991 A1 | 8/2003 | Halas et al. |
| 2003/0186295 A1 | 10/2003 | Colin et al. |
| 2003/0190608 A1 | 10/2003 | Blackburn et al. |
| 2003/0199081 A1 | 10/2003 | Wilding et al. |
| 2003/0211517 A1 | 11/2003 | Carulli et al. |
| 2004/0014202 A1 | 1/2004 | King et al. |
| 2004/0014238 A1 | 1/2004 | Krug et al. |
| 2004/0018116 A1 | 1/2004 | Desmond et al. |
| 2004/0018119 A1 | 1/2004 | Massaro |
| 2004/0022689 A1 | 2/2004 | Wulf et al. |
| 2004/0029258 A1 | 2/2004 | Heaney et al. |
| 2004/0029260 A1 | 2/2004 | Hansen et al. |
| 2004/0037739 A1 | 2/2004 | McNeely et al. |
| 2004/0053290 A1 | 3/2004 | Terbrueggen et al. |
| 2004/0063217 A1 | 4/2004 | Webster et al. |
| 2004/0065655 A1 | 4/2004 | Brown |
| 2004/0072278 A1 | 4/2004 | Chou et al. |
| 2004/0072375 A1 | 4/2004 | Gjerde et al. |
| 2004/0086427 A1 | 5/2004 | Childers et al. |
| 2004/0086956 A1 | 5/2004 | Bachur |
| 2004/0132059 A1 | 7/2004 | Scurati et al. |
| 2004/0141887 A1 | 7/2004 | Mainquist et al. |
| 2004/0151629 A1 | 8/2004 | Pease et al. |
| 2004/0157220 A1 | 8/2004 | Kurnool et al. |
| 2004/0161788 A1 | 8/2004 | Chen et al. |
| 2004/0189311 A1 | 9/2004 | Glezer et al. |
| 2004/0197810 A1 | 10/2004 | Takenaka et al. |
| 2004/0200909 A1 | 10/2004 | McMillan et al. |
| 2004/0209331 A1 | 10/2004 | Ririe |
| 2004/0209354 A1 | 10/2004 | Mathies et al. |
| 2004/0219070 A1 | 11/2004 | Handique |
| 2004/0224317 A1 | 11/2004 | Kordunsky et al. |
| 2004/0235154 A1 | 11/2004 | Oh et al. |
| 2004/0240097 A1 | 12/2004 | Evans |
| 2005/0009174 A1 | 1/2005 | Nikiforov et al. |
| 2005/0013737 A1 | 1/2005 | Chow et al. |
| 2005/0037471 A1 | 2/2005 | Liu et al. |
| 2005/0041525 A1 | 2/2005 | Pugia et al. |
| 2005/0042639 A1 | 2/2005 | Knapp et al. |
| 2005/0048540 A1 | 3/2005 | Inami et al. |
| 2005/0058574 A1 | 3/2005 | Bysouth et al. |
| 2005/0058577 A1 | 3/2005 | Micklash et al. |
| 2005/0064535 A1 | 3/2005 | Favuzzi et al. |
| 2005/0069898 A1 | 3/2005 | Moon et al. |
| 2005/0084424 A1 | 4/2005 | Ganesan et al. |
| 2005/0106066 A1 | 5/2005 | Saltsman et al. |
| 2005/0112754 A1 | 5/2005 | Yoon et al. |
| 2005/0121324 A1 | 6/2005 | Park et al. |
| 2005/0129580 A1 | 6/2005 | Swinehart et al. |
| 2005/0133370 A1 | 6/2005 | Park et al. |
| 2005/0135655 A1 | 6/2005 | Kopf-sill et al. |
| 2005/0142036 A1 | 6/2005 | Kim et al. |
| 2005/0152808 A1 | 7/2005 | Ganesan |
| 2005/0158781 A1 | 7/2005 | Woudenberg et al. |
| 2005/0170362 A1 | 8/2005 | Wada et al. |
| 2005/0186585 A1 | 8/2005 | Juncosa et al. |
| 2005/0196321 A1 | 9/2005 | Huang |
| 2005/0202470 A1 | 9/2005 | Sundberg et al. |
| 2005/0202489 A1 | 9/2005 | Cho et al. |
| 2005/0202504 A1 | 9/2005 | Anderson et al. |
| 2005/0208676 A1 | 9/2005 | Kahatt |
| 2005/0214172 A1 | 9/2005 | Burgisser |
| 2005/0220675 A1 | 10/2005 | Reed et al. |
| 2005/0227269 A1 | 10/2005 | Lloyd et al. |
| 2005/0233370 A1 | 10/2005 | Ammann et al. |
| 2005/0238545 A1 | 10/2005 | Parce et al. |
| 2005/0272079 A1 | 12/2005 | Burns et al. |
| 2005/0276728 A1 | 12/2005 | Muller-Cohn et al. |
| 2006/0041058 A1 | 2/2006 | Yin et al. |
| 2006/0057039 A1 | 3/2006 | Morse et al. |
| 2006/0057629 A1 | 3/2006 | Kim |
| 2006/0062696 A1 | 3/2006 | Chow et al. |
| 2006/0094108 A1 | 5/2006 | Yoder et al. |
| 2006/0113190 A1 | 6/2006 | Kurnik |
| 2006/0133965 A1 | 6/2006 | Tajima et al. |
| 2006/0134790 A1 | 6/2006 | Tanaka et al. |
| 2006/0148063 A1 | 7/2006 | Fauzzi et al. |
| 2006/0165558 A1 | 7/2006 | Witty et al. |
| 2006/0165559 A1 | 7/2006 | Greenstein et al. |
| 2006/0166233 A1 | 7/2006 | Wu et al. |
| 2006/0177376 A1 | 8/2006 | Tomalia et al. |
| 2006/0177855 A1 | 8/2006 | Utermohlen et al. |
| 2006/0183216 A1 | 8/2006 | Handique et al. |
| 2006/0201887 A1 | 9/2006 | Siddiqi |
| 2006/0205085 A1 | 9/2006 | Handique |
| 2006/0207944 A1 | 9/2006 | Siddiqi |
| 2006/0210435 A1 | 9/2006 | Alavie et al. |
| 2006/0223169 A1 | 10/2006 | Bedingham et al. |
| 2006/0228734 A1 | 10/2006 | Vann et al. |
| 2006/0246493 A1 | 11/2006 | Jensen et al. |
| 2006/0246533 A1 | 11/2006 | Fathollahi et al. |
| 2006/0269641 A1 | 11/2006 | Atwood et al. |
| 2006/0269961 A1 | 11/2006 | Fukushima et al. |
| 2007/0004028 A1 | 1/2007 | Lair et al. |
| 2007/0009386 A1 | 1/2007 | Padmanabhan et al. |
| 2007/0020699 A1 | 1/2007 | Carpenter et al. |
| 2007/0020764 A1 | 1/2007 | Miller |
| 2007/0026421 A1 | 2/2007 | Sundberg et al. |
| 2007/0042441 A1 | 2/2007 | Masters et al. |
| 2007/0048188 A1 | 3/2007 | Bigus |
| 2007/0054413 A1 | 3/2007 | Aviles et al. |
| 2007/0077648 A1 | 4/2007 | Okamoto et al. |
| 2007/0092901 A1 | 4/2007 | Ligler et al. |
| 2007/0098600 A1 | 5/2007 | Kayyem et al. |
| 2007/0099200 A1 | 5/2007 | Chow et al. |
| 2007/0104617 A1 | 5/2007 | Coulling et al. |
| 2007/0116613 A1 | 5/2007 | Elsener |
| 2007/0154895 A1 | 7/2007 | Spaid et al. |
| 2007/0177147 A1 | 8/2007 | Parce |
| 2007/0178607 A1 | 8/2007 | Prober et al. |
| 2007/0184463 A1 | 8/2007 | Molho et al. |
| 2007/0184547 A1 | 8/2007 | Handique et al. |
| 2007/0196237 A1 | 8/2007 | Neuzil et al. |
| 2007/0196238 A1 | 8/2007 | Kennedy et al. |
| 2007/0199821 A1 | 8/2007 | Chow |
| 2007/0215554 A1 | 9/2007 | Kreuwel et al. |
| 2007/0218459 A1 | 9/2007 | Miller et al. |
| 2007/0231213 A1 | 10/2007 | Prabhu et al. |
| 2007/0243626 A1 | 10/2007 | Windeyer et al. |
| 2007/0261479 A1 | 11/2007 | Spaid et al. |
| 2007/0269861 A1 | 11/2007 | Williams et al. |
| 2007/0292941 A1 | 12/2007 | Handique et al. |
| 2008/0000774 A1 | 1/2008 | Park et al. |
| 2008/0003649 A1 | 1/2008 | Maltezos et al. |
| 2008/0017306 A1 | 1/2008 | Liu et al. |
| 2008/0050804 A1 | 2/2008 | Handique et al. |
| 2008/0056948 A1 | 3/2008 | Dale et al. |
| 2008/0069729 A1 | 3/2008 | McNeely |
| 2008/0075634 A1 | 3/2008 | Herchenbach et al. |
| 2008/0090244 A1 | 4/2008 | Knapp et al. |
| 2008/0095673 A1 | 4/2008 | Xu |
| 2008/0118987 A1 | 5/2008 | Eastwood et al. |
| 2008/0124723 A1 | 5/2008 | Dale et al. |
| 2008/0149840 A1 | 6/2008 | Handique et al. |
| 2008/0160601 A1 | 7/2008 | Handique |
| 2008/0176230 A1 | 7/2008 | Owen et al. |

(56) References Cited

U.S. PATENT DOCUMENTS

| | | |
|---|---|---|
| 2008/0182301 A1 | 7/2008 | Handique et al. |
| 2008/0192254 A1 | 8/2008 | Kim et al. |
| 2008/0226502 A1 | 9/2008 | Jonsmann et al. |
| 2008/0240898 A1 | 10/2008 | Manz et al. |
| 2008/0247914 A1 | 10/2008 | Edens et al. |
| 2008/0262213 A1 | 10/2008 | Wu et al. |
| 2008/0280285 A1 | 11/2008 | Chen et al. |
| 2008/0308500 A1 | 12/2008 | Brassard |
| 2009/0047180 A1 | 2/2009 | Kawahara |
| 2009/0047713 A1 | 2/2009 | Handique |
| 2009/0066339 A1 | 3/2009 | Glezer et al. |
| 2009/0129978 A1 | 5/2009 | Wilson et al. |
| 2009/0130719 A1 | 5/2009 | Handique |
| 2009/0130745 A1 | 5/2009 | Williams et al. |
| 2009/0131650 A1 | 5/2009 | Brahmasandra et al. |
| 2009/0134069 A1 | 5/2009 | Handique |
| 2009/0136385 A1 | 5/2009 | Handique et al. |
| 2009/0136386 A1 | 5/2009 | Duffy et al. |
| 2009/0155123 A1 | 6/2009 | Williams et al. |
| 2009/0189089 A1 | 7/2009 | Bedingham et al. |
| 2009/0221059 A1 | 9/2009 | Williams et al. |
| 2009/0223925 A1 | 9/2009 | Morse et al. |
| 2009/0325164 A1 | 12/2009 | Vossenaar et al. |
| 2010/0009351 A1 | 1/2010 | Brahmasandra et al. |
| 2010/0120129 A1 | 5/2010 | Amshey et al. |
| 2010/0173393 A1 | 7/2010 | Handique et al. |
| 2010/0284864 A1 | 11/2010 | Holenstein et al. |
| 2011/0008825 A1 | 1/2011 | Ingber et al. |
| 2011/0027151 A1 | 2/2011 | Handique et al. |
| 2011/0097493 A1 | 4/2011 | Kerr et al. |
| 2011/0127292 A1 | 6/2011 | Sarofim et al. |
| 2011/0158865 A1 | 6/2011 | Miller et al. |
| 2011/0207140 A1 | 8/2011 | Handique et al. |
| 2011/0210257 A9 | 9/2011 | Handique et al. |
| 2011/0287447 A1 | 11/2011 | Norderhaug |
| 2011/0300033 A1 | 12/2011 | Battisti |
| 2012/0022695 A1 | 1/2012 | Handique et al. |
| 2012/0085416 A1 | 4/2012 | Ganesan |
| 2012/0122108 A1 | 5/2012 | Handique |
| 2012/0122231 A1 | 5/2012 | Tajima |
| 2012/0160826 A1 | 6/2012 | Handique |
| 2012/0171678 A1 | 7/2012 | Maltezos et al. |
| 2012/0171759 A1 | 7/2012 | Williams et al. |
| 2012/0183454 A1 | 7/2012 | Handique |
| 2012/0258463 A1 | 10/2012 | Duffy et al. |
| 2013/0037564 A1 | 2/2013 | Williams et al. |
| 2013/0071851 A1 | 3/2013 | Handique et al. |
| 2013/0096292 A1 | 4/2013 | Brahmasandra et al. |
| 2013/0101990 A1 | 4/2013 | Handique et al. |
| 2013/0164832 A1 | 6/2013 | Ganesan et al. |
| 2013/0183769 A1 | 7/2013 | Tajima |
| 2013/0217013 A1 | 8/2013 | Steel et al. |
| 2013/0217102 A1 | 8/2013 | Ganesan et al. |
| 2013/0251602 A1 | 9/2013 | Handique et al. |
| 2013/0280131 A1 | 10/2013 | Handique et al. |
| 2013/0288358 A1 | 10/2013 | Handique et al. |
| 2013/0315800 A1 | 11/2013 | Yin et al. |
| 2014/0030798 A1 | 1/2014 | Wu et al. |
| 2014/0045186 A1 | 2/2014 | Gubatayao et al. |
| 2014/0206088 A1 | 7/2014 | Lentz et al. |
| 2014/0212882 A1 | 7/2014 | Handique et al. |
| 2014/0227710 A1 | 8/2014 | Handique et al. |
| 2014/0297047 A1 | 10/2014 | Ganesan et al. |
| 2014/0323357 A1 | 10/2014 | Handique et al. |
| 2014/0323711 A1 | 10/2014 | Brahmasandra et al. |
| 2014/0329301 A1 | 11/2014 | Handique et al. |
| 2014/0342352 A1 | 11/2014 | Handique et al. |
| 2014/0377850 A1 | 12/2014 | Handique et al. |
| 2015/0064702 A1 | 3/2015 | Handique et al. |
| 2015/0118684 A1 | 4/2015 | Wu et al. |
| 2015/0133345 A1 | 5/2015 | Handique et al. |
| 2015/0142186 A1 | 5/2015 | Handique et al. |
| 2015/0152477 A1 | 6/2015 | Ganesan et al. |
| 2015/0174579 A1 | 6/2015 | Iten et al. |
| 2015/0315631 A1 | 11/2015 | Handique et al. |
| 2015/0328638 A1 | 11/2015 | Handique et al. |
| 2015/0376682 A1 | 12/2015 | Handique |
| 2016/0038942 A1 | 2/2016 | Roberts |
| 2016/0102305 A1 | 4/2016 | Brahmasandra et al. |
| 2016/0107161 A1 | 4/2016 | Lentz et al. |
| 2016/0250635 A1 | 9/2016 | Handique |
| 2016/0250640 A1 | 9/2016 | Williams et al. |
| 2016/0333337 A1 | 11/2016 | Duffy et al. |
| 2017/0097373 A1 | 4/2017 | Williams et al. |
| 2018/0017184 A1 | 1/2018 | Handique |
| 2018/0112252 A1 | 4/2018 | Handique |
| 2018/0119204 A1 | 5/2018 | Ganesan et al. |

FOREIGN PATENT DOCUMENTS

| | | |
|---|---|---|
| CN | 101466848 | 6/2009 |
| CN | 101522909 | 9/2009 |
| CN | 103540518 | 1/2014 |
| DE | 19929734 | 12/1999 |
| DE | 19833293 C1 | 1/2000 |
| EP | 0365828 A2 | 5/1990 |
| EP | 0483620 A2 | 5/1992 |
| EP | 0688602 A2 | 12/1995 |
| EP | 0766256 | 4/1997 |
| EP | 0772494 B1 | 5/1997 |
| EP | 1059458 A2 | 12/2000 |
| EP | 1077086 A2 | 2/2001 |
| EP | 1346772 A2 | 9/2003 |
| EP | 1541237 A2 | 6/2005 |
| EP | 1574586 A2 | 9/2005 |
| EP | 1745153 | 1/2007 |
| EP | 1780290 A2 | 5/2007 |
| EP | 1792656 A1 | 6/2007 |
| EP | 2372367 A1 | 10/2011 |
| FR | 2672301 | 8/1992 |
| FR | 2795426 | 12/2000 |
| GB | 2453432 A | 4/2009 |
| JP | S50-100881 | 8/1975 |
| JP | 58212921 A | 12/1983 |
| JP | S62-119460 | 5/1987 |
| JP | H01-502319 | 8/1989 |
| JP | H 03181853 | 8/1991 |
| JP | 04-053555 U | 5/1992 |
| JP | 06-064156 U | 9/1994 |
| JP | 07-020010 | 1/1995 |
| JP | H07-290706 | 11/1995 |
| JP | H08-122336 | 5/1996 |
| JP | H08-173194 | 7/1996 |
| JP | H08-211071 | 8/1996 |
| JP | H08-285859 | 11/1996 |
| JP | H09-325151 | 12/1997 |
| JP | 2001-502790 | 1/1998 |
| JP | H 11-501504 | 2/1999 |
| JP | H11-503315 | 3/1999 |
| JP | 2000-514928 | 4/1999 |
| JP | H11-156231 | 6/1999 |
| JP | H11-316226 | 11/1999 |
| JP | H11-515106 | 12/1999 |
| JP | 2000-180455 | 6/2000 |
| JP | 2000-266760 | 9/2000 |
| JP | 2000-275255 | 10/2000 |
| JP | 2001-502319 | 2/2001 |
| JP | 2001-204462 | 7/2001 |
| JP | 2001-509437 | 7/2001 |
| JP | 3191150 B2 | 7/2001 |
| JP | 2001-515216 | 9/2001 |
| JP | 2001-523812 | 11/2001 |
| JP | 2001-527220 | 12/2001 |
| JP | 2002-503331 | 1/2002 |
| JP | 2002-085961 | 3/2002 |
| JP | 2002-517735 | 6/2002 |
| JP | 2002-215241 | 7/2002 |
| JP | 2002-540382 | 11/2002 |
| JP | 2002-544476 | 12/2002 |
| JP | 2003-500674 | 1/2003 |
| JP | 2003-047839 A | 2/2003 |
| JP | 2003-047840 A | 2/2003 |
| JP | 2003-516125 | 5/2003 |
| JP | 2003-164279 | 6/2003 |

(56) References Cited

FOREIGN PATENT DOCUMENTS

| | | |
|---|---|---|
| JP | 2003-185584 | 7/2003 |
| JP | 2003-299485 | 10/2003 |
| JP | 2003-329693 | 11/2003 |
| JP | 2003-329696 | 11/2003 |
| JP | 2003-532382 A | 11/2003 |
| JP | 2004-003989 | 1/2004 |
| JP | 2004-506179 A | 2/2004 |
| JP | 2004-150797 A | 5/2004 |
| JP | 2004-531360 A | 10/2004 |
| JP | 2004-533838 | 11/2004 |
| JP | 2004-361421 | 12/2004 |
| JP | 2004-536291 | 12/2004 |
| JP | 2005-009870 | 1/2005 |
| JP | 2005-010179 | 1/2005 |
| JP | 2005-511264 | 4/2005 |
| JP | 2005-514718 | 5/2005 |
| JP | 2005-518825 | 6/2005 |
| JP | 2005-176613 A | 7/2005 |
| JP | 2005-192439 | 7/2005 |
| JP | 2005-192554 | 7/2005 |
| JP | 2005-204661 | 8/2005 |
| JP | 2005-525816 | 9/2005 |
| JP | 2005-291954 A | 10/2005 |
| JP | 2005-532043 | 10/2005 |
| JP | 2005-323519 | 11/2005 |
| JP | 2005-533652 | 11/2005 |
| JP | 2005-535904 | 11/2005 |
| JP | 2006-021156 A | 1/2006 |
| JP | 2006-094866 A | 4/2006 |
| JP | 2006-145458 | 6/2006 |
| JP | 2006-167569 | 6/2006 |
| JP | 2006-284409 | 10/2006 |
| JP | 2007-074960 | 3/2007 |
| JP | 2007-097477 | 4/2007 |
| JP | 2007-101364 | 4/2007 |
| JP | 2007-510518 | 4/2007 |
| JP | 2007-178328 | 7/2007 |
| JP | 2007-535933 | 12/2007 |
| JP | 2009-515140 | 4/2009 |
| JP | 2007-514405 A | 12/2009 |
| JP | 2009-542207 | 12/2009 |
| RU | 2418633 | 5/2011 |
| WO | WO 1998/006633 | 9/1988 |
| WO | WO 1990/012350 | 10/1990 |
| WO | WO 1992/005443 | 4/1992 |
| WO | WO 1994/011103 | 5/1994 |
| WO | WO 1996/004547 | 2/1996 |
| WO | WO 1996/018731 | 6/1996 |
| WO | WO 1997/005492 | 2/1997 |
| WO | WO 1997/021090 | 6/1997 |
| WO | WO 1998/000231 | 1/1998 |
| WO | WO 1998/022625 | 5/1998 |
| WO | WO 1998/35013 A1 | 8/1998 |
| WO | WO 1998/049548 | 11/1998 |
| WO | WO 1998/053311 | 11/1998 |
| WO | WO 1999/001688 | 1/1999 |
| WO | WO 1999/009042 | 2/1999 |
| WO | WO 1999/012016 | 3/1999 |
| WO | WO 1999/017093 | 4/1999 |
| WO | WO 1999/029703 | 6/1999 |
| WO | WO 1999/033559 | 7/1999 |
| WO | WO 2001/005510 | 1/2001 |
| WO | WO 2001/014931 | 3/2001 |
| WO | WO 2001/027614 | 4/2001 |
| WO | WO 2001/028684 | 4/2001 |
| WO | WO 2001/030995 | 5/2001 |
| WO | WO 2001/041931 | 6/2001 |
| WO | WO 2001/054813 | 8/2001 |
| WO | WO 2001/089681 | 11/2001 |
| WO | WO 2002/048164 | 6/2002 |
| WO | WO 2002/072264 | 9/2002 |
| WO | WO 2002/078845 | 10/2002 |
| WO | WO 2002/086454 | 10/2002 |
| WO | WO 2003/007677 | 1/2003 |
| WO | WO 2003/012325 | 2/2003 |
| WO | WO 2003/012406 | 2/2003 |
| WO | WO 2003/048295 | 6/2003 |
| WO | WO 2003/055605 | 7/2003 |
| WO | WO 2003/076661 | 9/2003 |
| WO | WO 2003/087410 | 10/2003 |
| WO | WO 2004/007081 | 1/2004 |
| WO | WO 2004/048545 | 6/2004 |
| WO | WO 2004/055522 | 7/2004 |
| WO | WO 2004/056485 | 7/2004 |
| WO | WO 2004/074848 | 9/2004 |
| WO | WO 2004/094986 | 11/2004 |
| WO | WO 2005/008255 | 1/2005 |
| WO | WO 2005/011867 | 2/2005 |
| WO | WO 2005/030984 | 4/2005 |
| WO | WO 2005/072353 | 8/2005 |
| WO | WO 2005/107947 | 11/2005 |
| WO | WO 2005/108571 | 11/2005 |
| WO | WO 2005/108620 | 11/2005 |
| WO | WO 2005/116202 | 12/2005 |
| WO | WO 2005/118867 | 12/2005 |
| WO | WO 2005/120710 | 12/2005 |
| WO | WO 2006/010584 | 2/2006 |
| WO | WO 2006/032044 | 3/2006 |
| WO | WO 2006/035800 | 4/2006 |
| WO | WO 2006/043642 | 4/2006 |
| WO | WO 2006/066001 | 6/2006 |
| WO | WO 2006/079082 | 7/2006 |
| WO | WO 2006/081995 | 8/2006 |
| WO | WO 2006/113198 | 10/2006 |
| WO | WO 2006/119280 | 11/2006 |
| WO | WO 2007/044917 | 4/2007 |
| WO | WO 2007/050327 | 5/2007 |
| WO | WO 2007/064117 | 6/2007 |
| WO | WO 2007/091530 | 8/2007 |
| WO | WO 2007/112114 | 10/2007 |
| WO | WO 2008/005321 | 1/2008 |
| WO | WO 2008/030914 | 3/2008 |
| WO | WO 2008/060604 | 5/2008 |
| WO | WO 2009/012185 | 1/2009 |
| WO | WO 2009/054870 | 4/2009 |
| WO | WO 2010/118541 | 10/2010 |
| WO | WO 2010/130310 | 11/2010 |
| WO | WO 2010/140680 | 12/2010 |
| WO | WO 2011/101467 | 8/2011 |

OTHER PUBLICATIONS

Kim et al., "Electrohydrodynamic Generation and Delivery of Monodisperse Picoliter Droplets Using a Poly(dimethylsiloxane) Microchip", Anal Chem. (2006) 78: 8011-8019.

Pal et al., "Phase Change Microvalve for Integrated Devices", Anal Chem. (2004) 76: 3740-3748.

Allemand et al., "pH-Dependent Specific Binding and Combining of DNA", Biophys J. (1997) 73(4): 2064-2070.

Bollet, C. et al., "A simple method for the isolation of chromosomal DNA from Gram positive or acid-fast bacteria", Nucleic Acids Research, vol. 19, No. 8 (1991), p. 1955.

Brahmasandra et al., On-chip DNA detection in microfabricated separation systems, SPIE Conference on Microfluidic Devices and Systems, 1998, vol. 3515, pp. 242-251, Santa Clara, CA.

Breadmore, M.C. et al., "Microchip-Based Purification of DNA from Biological Samples", Anal. Chem., vol. 75 (2003), pp. 1880-1886.

Brody, et al., Diffusion-Based Extraction in a Microfabricated Device, Sensors and Actuators Elsevier, 1997, vol. A58, No. 1, pp. 13-18.

Broyles et al., "Sample Filtration, Concentration, and Separation Integrated on Microfluidic Devices" Analytical Chemistry (American Chemical Society), (2003) 75(11): 2761-2767.

Burns et al., "An Integrated Nanoliter DNA Analysis Device", Science 282:484-487 (1998).

Carlen et al., "Paraffin Actuated Surface Micromachined Valve," in IEEE MEMS 2000 Conference, Miyazaki, Japan, (Jan. 2000) pp. 381-385.

Chung, Y. et al., "Microfluidic chip for high efficiency DNA extraction", Miniaturisation for Chemistry, Biology & Bioengineering, vol. 4, No. 2 (Apr. 2004), pp. 141-147.

(56) References Cited

OTHER PUBLICATIONS

Goldmeyer et al., "Identification of *Staphylococcus aureus* and Determination of Methicillin Resistance Directly from Positive Blood Cultures by Isothermal Amplification and a Disposable Detection Device", J Clin Microbiol. (Apr. 2008) 46(4): 1534-1536.
Handique et al, "Microfluidic flow control using selective hydrophobic patterning", SPIE, (1997) 3224:185-194.
Handique et al., "On-Chip Thermopneumatic Pressure for Discrete Drop Pumping", Anal. Chem., (2001) 73(8)1831-1838.
Handique et al., "Nanoliter-volume discrete drop injection and pumping in microfabricated chemical analysis systems", Solid-State Sensor and Actuator Workshop (Hilton Head, South Carolina, Jun. 8-11, 1998) pp. 346-349.
Handique et al., "Mathematical Modeling of Drop Mixing in a Slit-Type Microchannel", J. Micromesh. Microeng., 11:548-554 (2001).
Handique et al., "Nanoliter Liquid Metering in Microchannels Using Hydrophobic Patterns", Anal. Chem., 72(17):4100-4109 (2000).
Harding et al., "DNA isolation using Methidium-Spermine-Sepharose", Meth Enzymol. (1992) 216: 29-39.
Harding et al., "Rapid isolation of DNA from complex biological samples using a novel capture reagent—methidium-spermine-sepharose", Nucl Acids Res. (1989) 17(17): 6947-6958.
He, et al., Microfabricated Filters for Microfluidic Analytical Systems, Analytical Chemistry, American Chemical Society, 1999, vol. 71, No. 7, pp. 1464-1468.
Ibrahim, et al., Real-Time Microchip PCR for Detecting Single-Base Differences in Viral and Human DNA, Analytical Chemistry, American Chemical Society, 1998, 70(9): 2013-2017.
Khandurina et al., Microfabricated Porous Membrane Structure for Sample Concentration and Electrophoretic Analysis, Analytical Chemistry American Chemical Society, 1999, 71(9):1815-1819.
Kopp et al., Chemical Amplification: Continuous-Flow PCR on a Chip, www.sciencemag.org, 1998, vol. 280, pp. 1046-1048.
Kuo et al., "Remnant cationic dendrimers block RNA migration in electrophoresis after monophasic lysis", J Biotech. (2007) 129: 383-390.
Kutter et al., Solid Phase Extraction on Microfluidic Devices, J. Microcolumn Separations, John Wiley & Sons, Inc., 2000, 12(2): 93-97.
Labchem; Sodium Hydroxide, 0,5N (0.5M); Safety Data Sheet, 2015; 8 pages.
Lagally et al., Single-Molecule DNA Amplification and Analysis in an Integrated Microfluidic Device, Analytical Chemistry, American Chemical Society, 2001, 73(3): 565-570.
Livache et al., "Polypyrrole DNA chip on a Silicon Device: Example of Hepatitis C Virus Genotyping", Analytical Biochemisty, (1998) 255: 188-194.
Mascini et al., "DNA electrochemical biosensors", Fresenius J. Anal. Chem., 369: 15-22, (2001).
Meyers, R.A., Molecular Biology and Biotechnology: A Comprehensive Desk Reference; VCH Publishers, Inc. New York, NY; (1995) pp. 418-419.
Nakagawa et al., Fabrication of amino silane-coated microchip for DNA extraction from whole blood, J of Biotechnology, Mar. 2, 2005, 116: 105-111.
Northrup et al., A Miniature Analytical Instrument for Nucleic Acids Based on Micromachined Silicon Reaction Chambers Analytical Chemistry, American Chemical Society 1998, 70(5) 918-922.
Oleschuk et al., Trapping of Bead-Based Reagents within Microfluidic Systems: On-Chip Solid-Phase Extraction and Electrochromatography, Analytical Chemistry, American Chemical Society, 2000, 72(3): 585-590.
Plambeck et al., "Electrochemical Studies of Antitumor Antibiotics", J. Electrochem Soc.: Electrochemical Science and Technology (1984), 131(11); 2556-2563.
Roche et al. "Ectodermal commitment of insulin-producing cells derived from mouse embryonic stem cells" Faseb J (2005) 19: 1341-1343.
Ross et al., Analysis of DNA Fragments from Conventional and Microfabricated PCR Devices Using Delayed Extraction MALDI-TOF Mass Spectrometry, Analytical Chemistry, American Chemical Society, 1998, 70(10): 2067-2073.
Shoffner et al., Chip PCR.I. Surface Passivation of Microfabricated Silicon-Glass Chips for PCR, Nucleic Acids Research, Oxford University Press, (1996) 24(2): 375-379.
Smith, K. et al., "Comparison of Commercial DNA Extraction Kits for Extraction of Bacterial Genomic DNA from Whole-Blood Samples", Journal of Clinical Microbiology, vol. 41, No. 6.
Tanaka et al., "Modification of DNA extraction from maize using polyamidoamine-dendimer modified magnetic particles", Proceedings of the 74th Annual Meeting of the Electrochemical Society of Japan, Mar. 29, 2007; Faculty of Engineering, Science University of Tokyo; 2 pages.
Wang, "Survey and Summary, from DNA Biosensors to Gene Chips", Nucleic Acids Research, 28(16):3011-3016 (2000).
Waters et al., Microchip Device for Cell Lysis, Multiplex PCR Amplification, and Electrophoretic Sizing, Analytical Chemistry, American Chemical, American Chemical Society, 1998, 70(1): 158-162.
Weigl, et al., Microfluidic Diffusion-Based Separation and Detection, www.sciencemag.org, 1999, vol. 283, pp. 346-347.
Wu et al., "Polycationic dendrimers interact with RNA molecules: polyamine dendrimers inhibit the catalytic activity of Candida ribozymes", Chem Commun. (2005) 3: 313-315.
Yoza et al., "Fully Automated DNA Extraction from Blood Using Magnetic Particles Modified with a Hyperbranched Polyamidoamine Dendrimer", J Biosci Bioeng, 2003, 95(1): 21-26.
Yoza et al., DNA extraction using bacterial magnetic particles modified with hyperbranched polyamidoamine dendrimer, J Biotechnol., Mar. 20, 2003, 101(3): 219-228.
Zhou et al., "Cooperative binding and self-assembling behavior of cationic low molecular-weight dendrons with RNA molecules", Org Biomol Chem. (2006) 4(3): 581-585.
Zhou et al., "PAMAM dendrimers for efficient siRNA delivery and potent gene silencing", Chem Comm.(Camb.) (2006) 22:2362-2364.
International Search Report and Written Opinion dated Jan. 7, 2013 for Application No. PCT/US2012/058102, filed Sep. 28, 2012.
International Preliminary Report on Patentability dated Apr. 1, 2014 for Application No. PCT/US2012/058102, filed Sep. 28, 2012.
Oh K.W. et al., "A Review of Microvalves", J Micromech Microeng. (2006) 16:R13-R39.

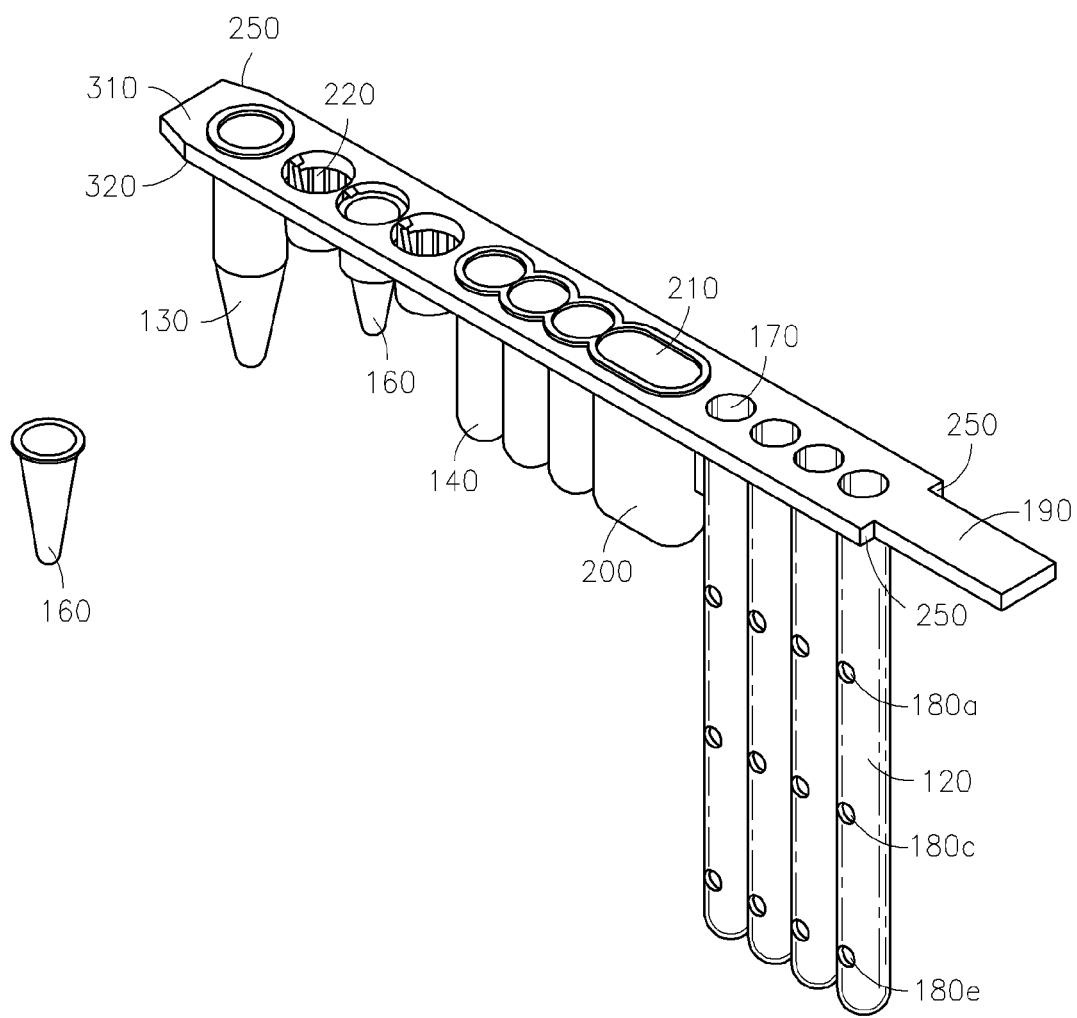
FIG.IB

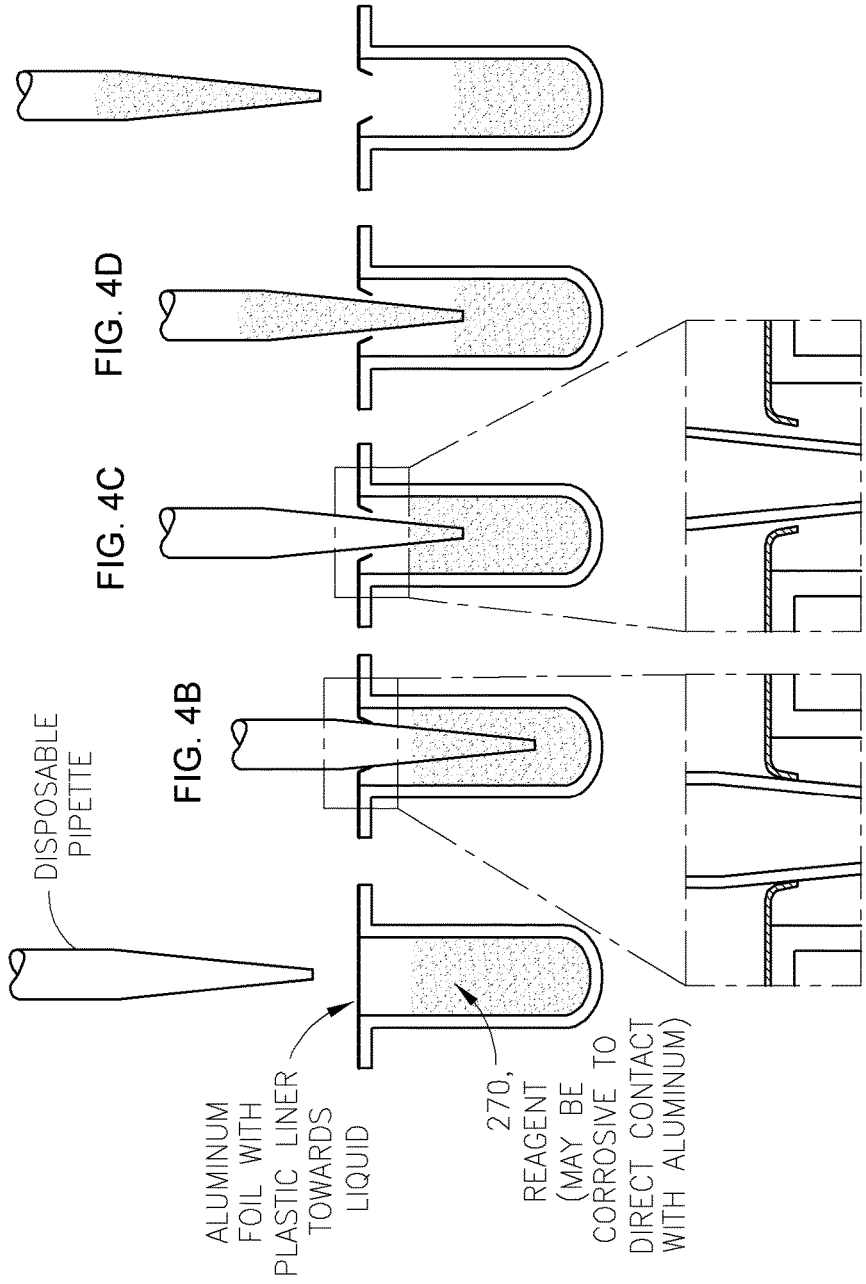

UNITIZED REAGENT STRIP

CROSS REFERENCE TO RELATED APPLICATIONS

The present application is a continuation of U.S. application Ser. No. 14/974,624, filed Dec. 18, 2015 and scheduled to issue as U.S. Pat. No. 9,480,983 on Nov. 1, 2016, which is a continuation of U.S. application Ser. No. 14/227,883, filed Mar. 27, 2014 and issued as U.S. Pat. No. 9,222,954 on Dec. 29, 2015, which is a continuation of International Application No. PCT/US2012/058102, filed Sep. 28, 2012, which claims priority to U.S. Provisional Application Ser. No. 61/541,991, entitled "UNITIZED REAGENT STRIP," filed Sep. 30, 2011. The disclosures of all of the above-referenced prior applications, publications, and patents are considered part of the disclosure of this application, and are incorporated by reference herein in their entirety.

BACKGROUND

Technical Field

The technology described herein generally relates to holders for reagents and disposables, such as may be used for transporting the reagents and for carrying out processing operations with the reagents. e.g., in automated sample preparation/processing devices.

Background

Automation of diagnostic assays and high throughput screening has become more prevalent, and several devices have been developed to meet the growing need for quick, sensitive, and consistent analysis of multiple samples. For example, in recent years, integrated devices in which sample preparation and processing, e.g., for nucleic acid assays, have been developed.

Many important assays require the isolation of various components, such as nucleic acids, proteins, or the like, from clinical and/or environmental samples. Isolating nucleic acids, proteins, or other analytes of interest from clinical or environmental samples can be time consuming and labor intensive. Manual preparation of samples is also subject to more variation due to human error and inaccuracies. Several variables that affect the consistency and accuracy of sample preparation, which typically involves several reagents and the need for multiple transfer (e.g., pipetting) operations. Often, required reagents are of sufficient variety that they typically require different handling from one another and are available from different vendors. As such, the variation between different vendors and lots of a particular reagent, and different handling of various reagents by one or many individuals, can lead to assay variability. Second, multiple pipetting operations introduces the possibility of cross-contamination, e.g., inter-sample and intra-sample, (e.g., the reagents used during different preparation and/or processing steps of a single sample).

There is a need for methods and devices of carrying out preparation and processing of large numbers of samples in parallel, and that minimize inter-assay variability. Desirably, the methods and devices would minimize user manipulation of reagents and/or disposables used in the preparation and processing procedures, to enable efficient sample processing and minimize both contamination and imprecision, and that would maintain flexibility.

The discussion of the background herein is included to explain the context of the inventions described herein. This is not to be taken as an admission that any of the material referred to was published, known, or part of the common general knowledge as at the priority date of any of the claims.

BACKGROUND

Provided herein are unitized reagent strips, and methods of using the same. In one aspect, provided is a unitized reagent strip, comprising: a strip with a top side and a bottom side, comprising: a first and a second pipette sheath comprising a opposing sides, said first and second pipette sheaths comprising a first and second pipette tip aperture, respectively, each of which comprises a separate opening on the top side of the strip, and wherein said first and second pipette tip apertures are configured for insertion of a first and second pipette tip into said first and second pipette sheaths, respectively, and wherein each of said first and second pipette sheaths is configured to substantially surround the length of a first and second pipette tip, respectively; a process tube; and a receptacle, comprising an opening through the reagent strip, wherein said receptacle is configured to receive a reagent tube.

In another aspect, provided herein is a method of detecting the presence or absence of a pipette tip within a pipette sheath of a unitized reagent strip, comprising: a strip with a top side and a bottom side, comprising: a first and a second pipette sheath comprising a opposing sides, said first and second pipette sheaths comprising a first and second pipette tip aperture, respectively, each of which comprises a separate opening on the top side of the strip, and wherein said first and second pipette tip apertures are configured for insertion of a first and second pipette tip into said first and second pipette sheaths, respectively, and wherein each of said first and second pipette sheaths is configured to substantially surround the length of a first and second pipette tip, respectively; a process tube; and a receptacle, comprising an opening through the reagent strip, wherein said receptacle is configured to receive a reagent tube, wherein said first pipette sheath comprises an aperture pair, said aperture pair comprising the first cored hole and a second cored hole extending through the sidewall of the first pipette sheath, wherein the first and second cored holes are located on opposing sides of the sidewall of the first pipette sheath, and are positioned at the same distance along the length of the first pipette sheath from the first pipette tip aperture; providing an optical beam through the first cored hole of said pipette sheath aperture pair; and detecting whether said optical beam exits unobstructed through said second cored hole of said first pipette sheath aperture pair, wherein the unobstructed exit of said optical beam through said second cored hole of said first pipette sheath is indicative of the absence of the pipette tip within the pipette sheath, and wherein obstructed exit of said optical beam though said second cored hole indicates the presence of the pipette tip within said first pipette sheath.

In another aspect, provided herein is a method of determining the length of a pipette tip within a pipette sheath of a unitized reagent strip, comprising: providing a unitized reagent strip comprising: a strip with a top side and a bottom side, said strip comprising: a process tube; a receptacle, comprising an opening through the reagent strip, wherein said receptacle is configured to receive a reagent tube; a first and a second pipette sheath, each of said pipette sheaths comprising: a first and second pipette tip aperture, respectively, each of which comprises a separate opening on the top side of the strip, and wherein said first and second pipette tip apertures are configured for insertion of a first and second pipette tip into said first and second pipette sheaths, respectively, and wherein each of said first and second pipette sheaths is configured to substantially surround the length of a first and second pipette tip, respectively; a top pipette sheath aperture pair and a bottom pipette sheath aperture pair within said first pipette sheath, said top and bottom aperture pairs each comprising a first and a second cored hole extending through a sidewall of the first pipette sheath, wherein the first and second cored holes of said top and bottom pipette sheath aperture pairs are located on opposite sides of the first pipette sheath, and positioned at the same distance along the length of the first pipette sheath from the first pipette tip aperture, and wherein said top pipette sheath aperture pair is located more proximal to the first pipette tip aperture than said bottom pipette sheath aperture pair; providing an optical beam through said first cored hole of said top pipette sheath aperture pair; providing an optical beam through said first cored hole of said bottom pipette sheath aperture pair; detecting whether said optical beam is obstructed from passing through said second cored hole of said top pipette sheath aperture pair; and detecting whether said optical beam is obstructed from passing through said bottom cored hole of said first pipette sheath aperture pair, wherein obstruction of said optical beam through the second cored hole of the top aperture pair and passage of said optical beam through said second cored hole of said bottom pipette sheath aperture pair indicates that the pipette tip within said first pipette sheath has a length that does not extend down to the bottom pipette sheath aperture pair when inserted into the first pipette sheath.

In yet another aspect, provided is a method of determining the length of a pipette tip within a pipette sheath of a unitized reagent strip, comprising: providing a unitized reagent strip comprising: a strip with a top side and a bottom side, said strip comprising: a process tube; a receptacle, comprising an opening through the reagent strip, wherein said receptacle is configured to receive a reagent tube; a first and a second pipette sheath, each pipette sheath comprising: a first and second pipette tip aperture, respectively, each of which comprises a separate opening on the top side of the strip, and wherein said first and second pipette tip apertures are configured for insertion of a first and second pipette tip into said first and second pipette sheaths, respectively, and wherein each of said first and second pipette sheaths is configured to substantially surround the length of a first and second pipette tip, respectively; a top pipette sheath aperture pair and a bottom pipette sheath aperture pair within said first pipette sheath, said top and bottom aperture pairs each comprising a first and a second cored hole extending through a sidewall of the first pipette sheath, wherein the first and second cored holes of said top and bottom pipette sheath aperture pairs are located on opposite sides of the first pipette sheath, and positioned at the same distance along the length of the pipette sheath from the pipette tip aperture, and wherein said top pipette sheath aperture pair is located more proximal to the first pipette tip aperture than said bottom pipette sheath aperture pair; providing an optical beam through said first cored hole of said top pipette sheath aperture pair; providing an optical beam through said first cored hole of said bottom pipette sheath aperture pair; detecting whether said optical beam is obstructed from passing through said second cored hole of said top pipette sheath aperture pair; and detecting whether said optical beam is obstructed from passing through said bottom cored hole of said first pipette sheath aperture pair, wherein obstruction of said optical beam through the second cored hole of the top aperture pair and passage of said optical beam through said second cored hole of said bottom pipette sheath aperture pair indicates that the pipette tip within said pipette sheath has a length that does not extend down to the bottom pipette sheath aperture pair when inserted into the pipette sheath.

In still another aspect, provided herein is a method of determining the length of a pipette tip within a pipette sheath of a unitized reagent strip, comprising: providing a unitized reagent strip comprising: a strip with a top side and a bottom side, said strip comprising: a process tube; a receptacle, comprising an opening through the reagent strip, wherein said receptacle is configured to receive a reagent tube; a first and a second pipette sheath, each comprising: a first and second pipette tip aperture, respectively, each of which comprises a separate opening on the top side of the strip, and wherein said first and second pipette tip apertures are configured for insertion of a first and second pipette tip into said first and second pipette sheaths, respectively, and wherein each of said first and second pipette sheaths is configured to substantially surround the length of a first and second pipette tip, respectively; a top cored hole and a bottom cored within said first pipette sheath, said top and bottom cored holes each extending through a sidewall of the pipette sheath, wherein said top cored hole is located more proximal to the first pipette tip aperture than said bottom cored hole; determining whether a pipette tip extends within said first pipette sheath from the first pipette tip aperture to the distance of the first cored hole; and determining whether a pipette tip extends within said first pipette sheath from the first pipette tip aperture to the distance of the second cored hole.

BRIEF DESCRIPTION OF THE DRAWINGS

One or more various embodiments provided herein is described in detail with reference to the following figures. The drawings are provided for purposes of illustration only and merely depict typical or example embodiments of the invention. These drawings are provided to facilitate the reader's understanding of the invention and shall not be considered limiting of the breadth, scope, or applicability of the invention. It should be noted that for clarity and ease of illustration these drawings are not necessarily made to scale.

Some of the figures included herein illustrate various embodiments of the invention from different viewing angles. Although the accompanying descriptive text may refer to such views as "top," "bottom" or "side" views, such references are merely descriptive and do not imply or require that the invention be implemented or used in a particular spatial orientation unless explicitly stated otherwise.

These and other features and advantages of the various embodiments disclosed herein will be better understood with respect to the following description and drawings, in which like numbers refer to like parts throughout, and in which:

FIG. 1A is a perspective view of a reagent strip as described herein.

FIG. 1B is a perspective view of the reagent strip as described herein, with reagent tube (160) shown separate from and inserted in the strip.

FIG. 1C is a cutaway view of the process tube in section A-A from FIG. 1A.

FIG. 1D is a cutaway view of the reagent tube 140 in section B-B from FIG. 1A.

FIG. 1E is a cutaway view of the pipette sheath in section C-C from FIG. 1A.

FIG. 1F is a top view of the reagent strip of FIG. 1A.

FIG. 1G is a bottom view of the reagent strip of FIG. 1A.

FIG. 1H is a cutaway view of one embodiment of the reagent strip of FIG. 1A.

FIG. 2A is a perspective view of a reagent strip as described herein.

FIG. 2B is a top view of the reagent strip of FIG. 2A.

FIG. 2C is a bottom view of the reagent strip of FIG. 2A.

Figure 3:
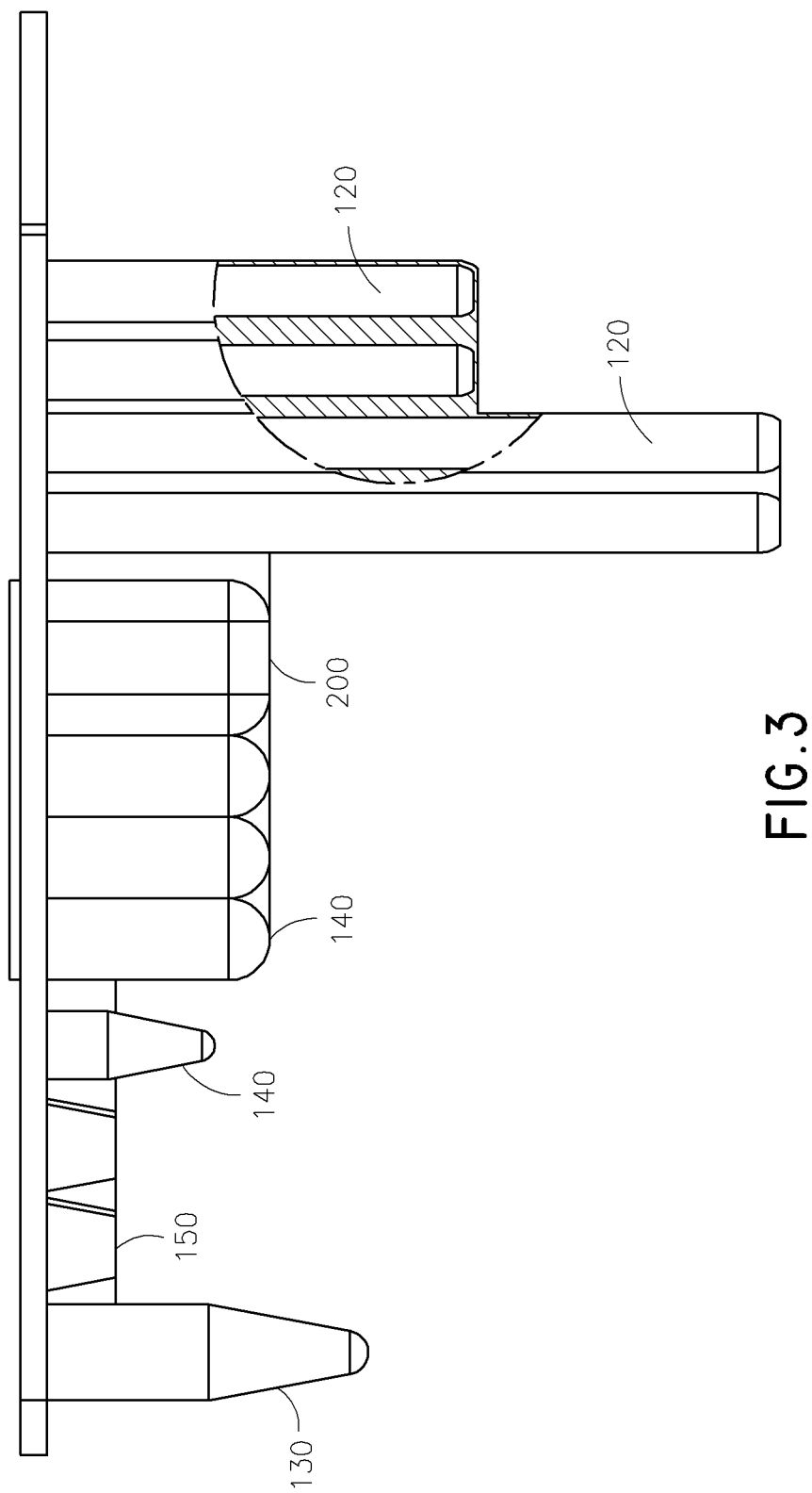

FIG. 3 is a plan view of a reagent strip as described herein.

FIGS. 4A-4E show a sequence of pipetting operations in conjunction with a laminated layer.

Figure 5A:
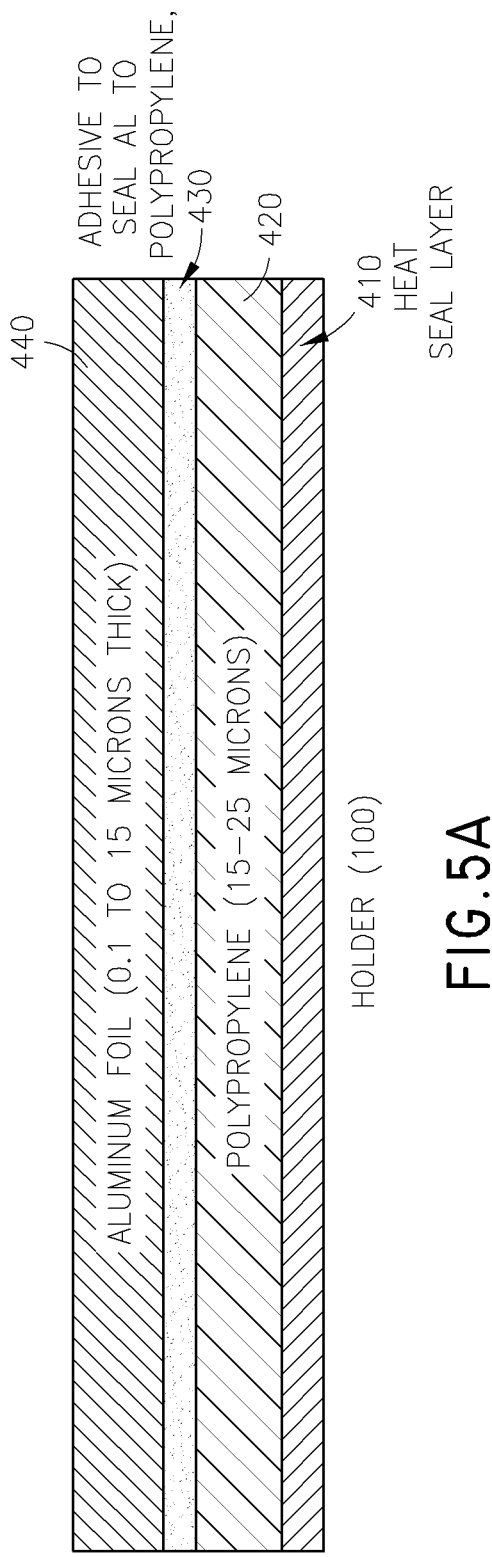
Figure 5B:
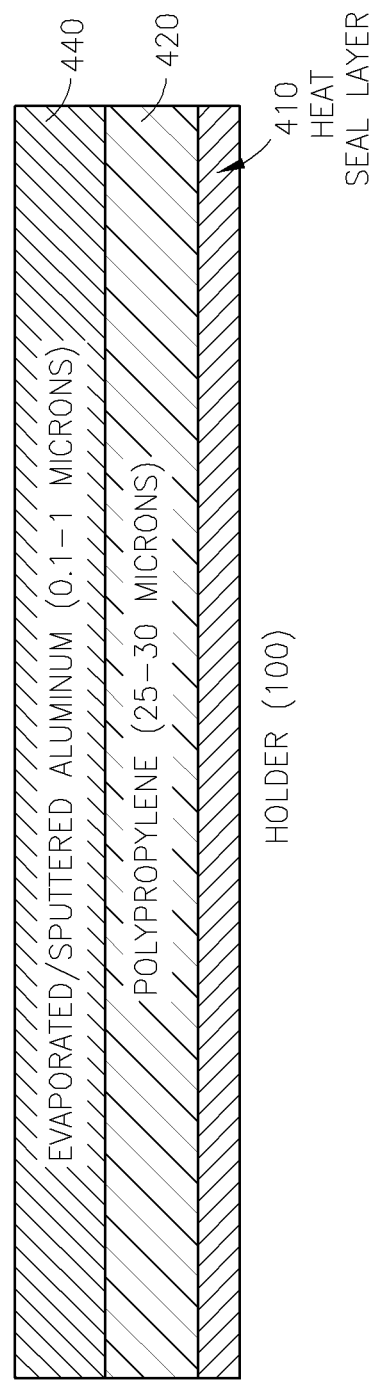

FIGS. 5A and 5B show embodiments of a laminated layer.

DETAILED DESCRIPTION OF THE PREFERRED EMBODIMENT

The embodiments described herein provide reagent holders that are configured to hold, transport, and store a plurality of reagents and materials used in the preparation and processing of samples, e.g., clinical and/or environmental samples. The reagent holders provided herein provide several advantages in the preparation and processing of samples, such as clinical and/or environmental samples, and are suitable for use with automated sample processing devices. By way of example, some of the advantages provided by the reagent holders disclosed herein include, but are not limited to a design that (1) minimizes of cross-contamination of reagents and samples; (2) facilitates quality control of the strips/disposables; (3) simplifies manufacture; and (4) provides versatility useful for different molecular platforms and automated devices.

The holders herein are also configured for use by an apparatus that carries out automated sample preparation, for example, on multiple samples simultaneously. An exemplary form of such an apparatus is described, e.g., in International Patent Application Publication. No. WO 09/054870, incorporated herein by reference in its entirety.

Preparation of a sample for use in assays, such as nucleic acid testing ("NAT"), e.g., by PCR or the like, can include one or more of the following steps: contacting a polynucleotide sample with a nucleic acid testing NAT reagent mixture, e.g., in the case of PCR or other amplification, which comprises a polymerase enzyme and a plurality of nucleotides. In some embodiments, the reagent mixtures can further comprise hybridization probes with detectable moieties, wherein the probes specifically hybridize to target nucleic acids (and/or positive control target nucleic acid sequences).

In some embodiments, the reagent mixture can be in the form of one or more lyophilized pellets, as stored in a reagent tube on the holder, and the method can further include reconstituting the reagent pellet with liquid to create a PCR reagent mixture solution. The holder herein provides in a self-contained manner, all of the reagents required to prepare a nucleic acid testing-ready sample, or, when delivered to a user in kit form, contains in conjunction with other packages all of the required reagents. Suitable reagents, and protocols for using the same in DNA and RNA extractions can be found in, respectively, U.S. Patent Application Publication Nos. US 2010-0009351, and US 2009-0131650, each of which is herein incorporated by reference.

Several features of the reagent holders described herein are described with reference to the drawings provided herein. The exemplary holders shown in FIGS. 1A-H, 2A-C, and 3, can each be referred to as a "unitized disposable strip", or a "unitized strip", because they are intended to be used as a single unit that is configured to hold all of the reagents and receptacles necessary to perform a sample preparation, and because they are laid out in a strip format. It is consistent with the description herein, though, that other geometric arrangements of the various receptacles are contemplated, so that the description is not limited to a linear, or strip, arrangement, but can include a circular or grid arrangement.

Figure 1A:
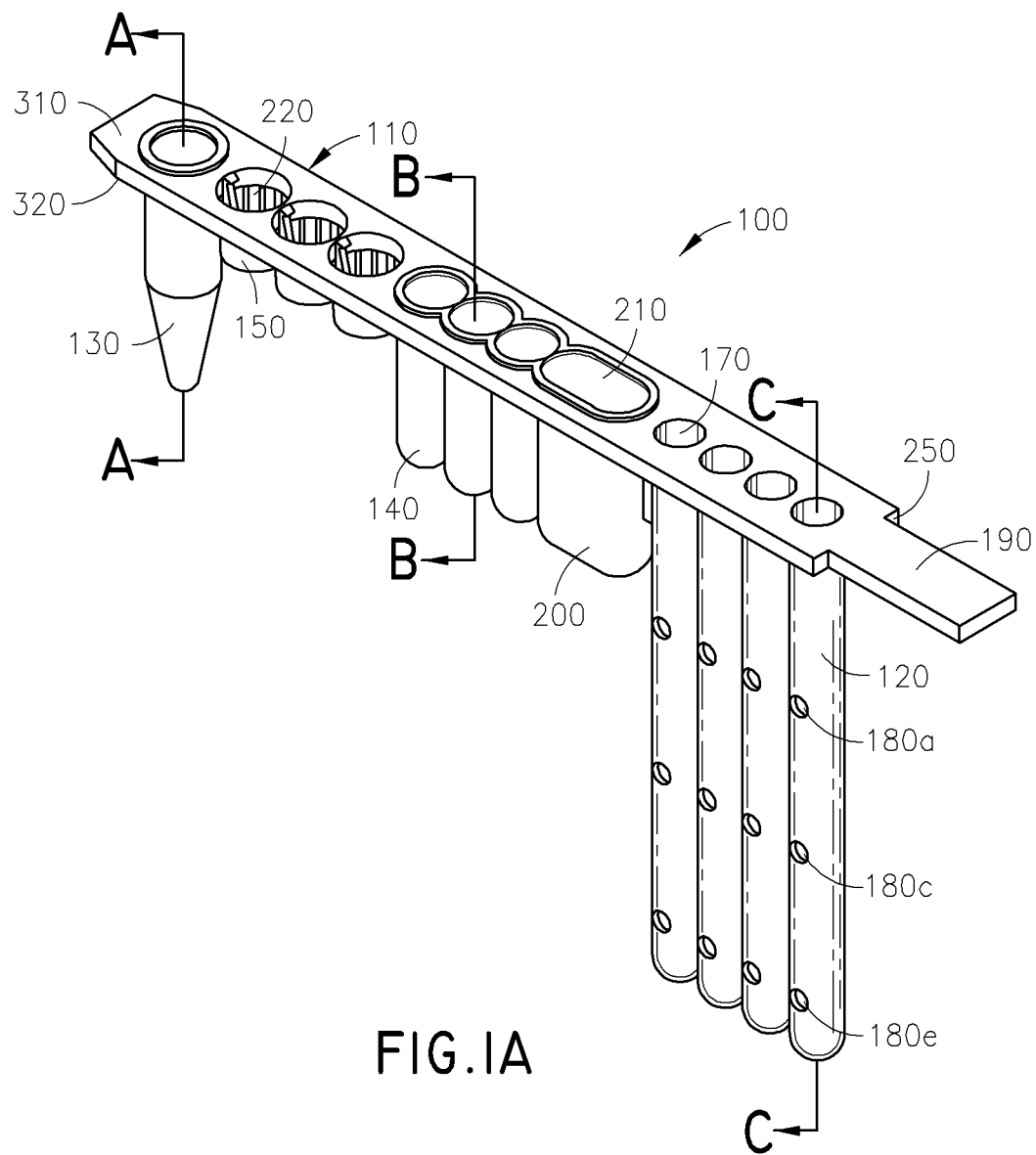
Figure 1C:
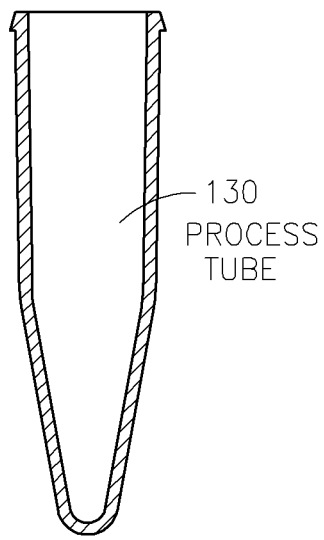
Figure 1D:
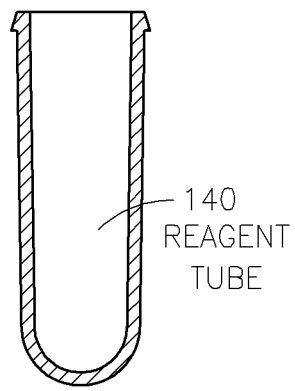
Figure 1E:
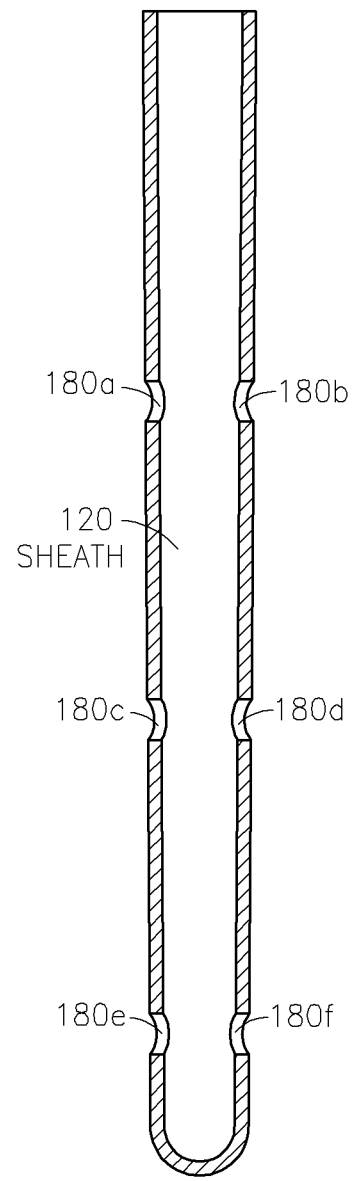
Figure 1F:
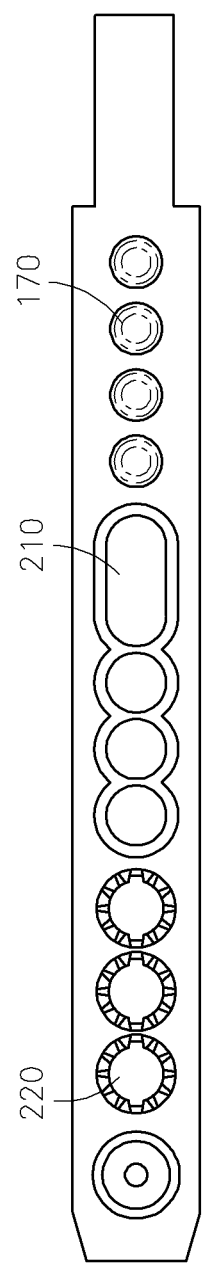
Figure 1G:
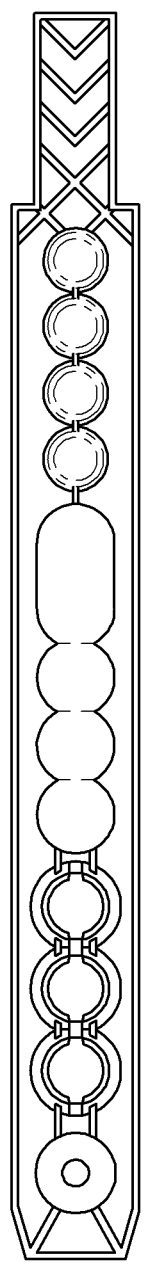
Figure 1H:
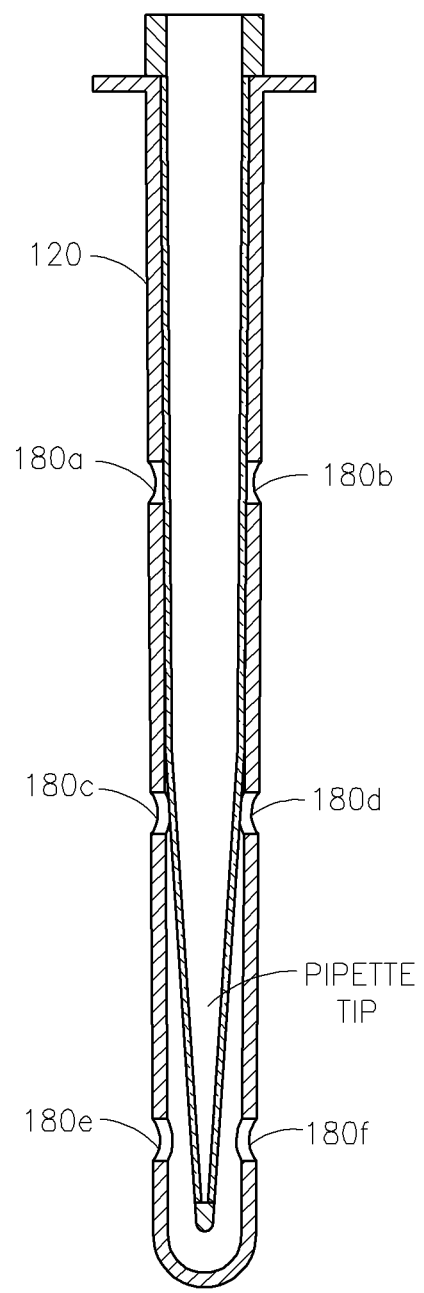
Figure 2A:
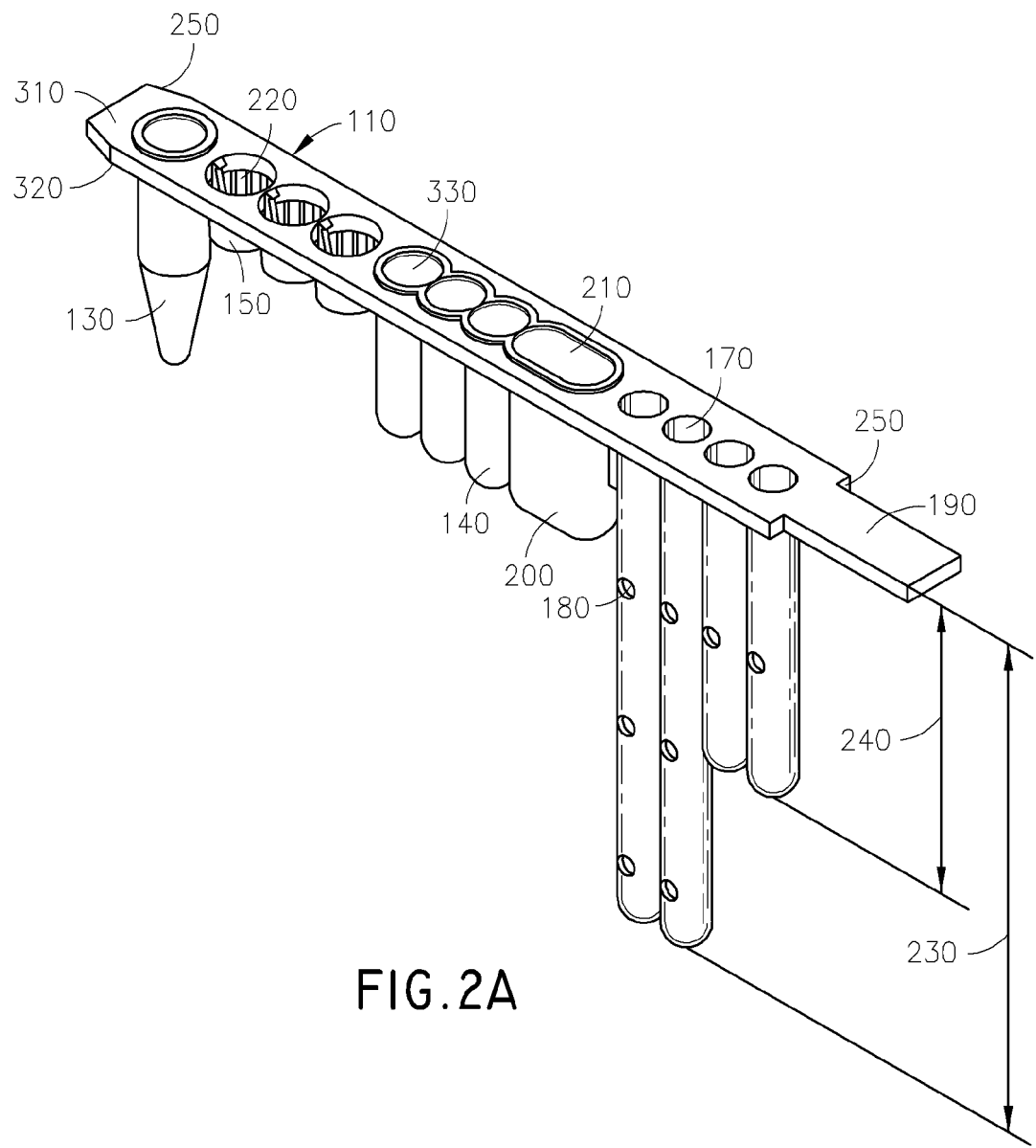
Figure 2B:
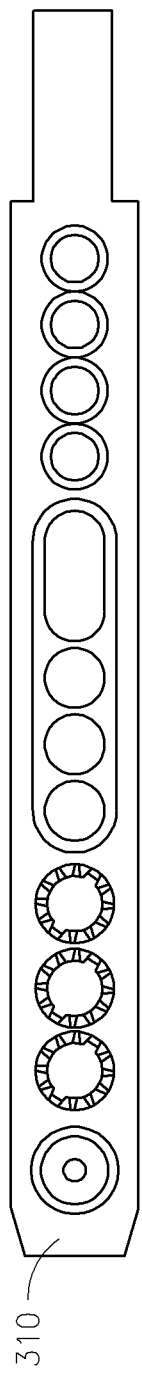

Turning to FIGS. 1-3, shown are exemplary reagent strips 100. Reagent strip 100 comprises a strip 110, that has both a top side 310 and a bottom side 320, and that houses various components used in sample preparation and/or processing, including one or more pipette sheaths 120, one or more process tubes 130, and which also houses one or more integral reagent tubes 140 having reagent tube apertures 330. In some embodiments, the reagent tubes 140 are integral/unitary with the strip 110. In some embodiments, the process tubes 130 are integral with the strip 110. In some embodiments, the process tubes 130 are separate from the unitized strip. In some embodiments, the reagent strip comprises one or more tube receptacles 150. The tube receptacles 150 can be integral/unitary with the strip 110, and are configured to receive one or more reagent tubes 160 that are not integral/unitary with the strip 110. In some embodiments, reagent tubes 160 can be integral with the strip, as shown in FIG. 2A.

By way of example, unitized reagent strips as described herein can include, for example, 1, 2, 3, 4, 5, 6, 7, 8, 9, 10, or more pipette sheaths, 1, 2, 3, 4, 5, 6, 7, 8, 9, 10, or more process tubes, 1, 2, 3, 4, 5, 6, 7, 8, 9, 10, or more receptacles, 1, 2, 3, 4, 5, 6, 7, 8, 9, 10, or more integral reagent tubes, 1, 2, 3, 4, 5, or more waste containers, or the like, organized in any configuration on the strip.

In preferred embodiments, the reagent strip comprises one or more pipette sheaths 120 that are substantially separated from adjacent pipette sheaths and/or adjacent reagent tubes 140, process tubes 130, or tube receptacles 150. Preferably, the pipette sheaths 120 are integral with the strip 110, and thus do not require manual assembly onto the strip 110. Individual pipette tips can be inserted into individual pipette sheaths 120, by virtue of individual pipette tip apertures 170 that are present in the strip 110. The pipette sheaths 120 substantially surround the sides and bottoms of individual pipette tips. The term "substantially surrounding", when used in reference to the pipette sheaths, means that the sheath surrounds at least the main body of the pipette tip. That is, the top of the pipette tip may comprise a lip, or the like, at the top portion of the pipette tip (through which the pipettor is inserted), that extends past (and possibly rests on top of), the top portion of the strip 110. In some embodiments, the pipette sheath surrounds, e.g., 70%, 80%, 85%, 80%, 90%, 95%, or more, of the length of a pipette tip. By substantially surrounding individual pipette tips, the pipette sheaths prevent contact between each pipette tip and other pipette tips, reagent tubes, process tubes, waste containers, or the like, present in the strip. Specifically, each pipette sheath is configured to have material surrounding, or forming a barrier or wall 290 that isolates the body of a pipette tip inserted therein, from other reagents/holders or disposables (e.g., other pipette tips) within the unitized strip. Thus, the individual pipette sheaths prevent any cross-contamination between reagents and/or samples that are manipulated during preparation and/or processing by pipetting. For example, the pipette sheaths 120 prevent contamination between adjacent pipette tips on the same strip, as well as between pipette tips housed in reagent strips held in adjacent position, e.g., within an automated sample preparation/processing device.

In some embodiments, the pipette sheaths contain one or more sheath apertures, or cored holes 180. In some embodiments, the cored holes 180 are present as pairs of sheath apertures. whereas in other embodiments, the cored holes are not part of an aperture pair. In some embodiments, the pipette sheaths comprise one, two, three, four, five, six, seven, eight, nine, ten, or more, unpaired cored holes 180. In some embodiments, the pipette sheaths comprise a plurality of aperture pairs, wherein each pipette sheath aperture pair comprises two cored holes 180. For example, a pipette sheath can include e.g., one pair, two pairs, three pairs, four pairs, five pairs, six pairs, seven pairs, eight pairs, nine pairs, ten pairs, or more, of sheath aperture pairs. Pipette sheath aperture pairs comprise a first cored hole 180a and a second cored hole 180b, which are present on opposing sides of, and equidistant from the top of, the pipette sheath 120, as shown e.g., in FIG. 1D. In some embodiments, unpaired cored holes 180 can be present on opposing sides of, and at various distances from the top of, the pipette sheath 120.

The cored holes 180, whether present unpaired, or as an aperture pair(s), can advantageously be used to determine the presence or absence of a pipette tip within a pipette sheath 120, either manually (by visual inspection), or automatically (e.g., by an optical sensor). The cored holes 180 thereby provide an additional quality control checkpoint prior to use of the unitized reagent strip. For example, in the context of automated detection of pipette tips, when cored holes 180 are present as a pipette sheath aperture pair, one can pass light through the first cored hole of the pair. When the pipette sheath 120 is not housing a pipette tip, light can pass through the first and second cored holes of the aperture pair aligned on opposing sides of the sheath. When a pipette tip is present within the sheath, the pipette tip blocks or obstructs visible pathway between the first and second cored holes of each aperture pair. In this manner, the sheath aperture pairs 180 can be readily used to determine whether or not a pipette tip is present in each sheath 120. When cored holes 180 are present, but not part of a pipette sheath aperture pair, one can determine the presence or absence of a pipette tip within the sheath by calculating, e.g., the reflection or obstruction of light passed through the unpaired cored hole, as the reflection or obstruction will differ depending upon whether a pipette tip is present within the pipette sheath or is absent. For example, in some embodiments, detection of light reflection may be determined using art recognized means and devices such as retro-reflective detectors. In some embodiments, the presence or absence of a pitpette tip in a sheath is determined by measuring the obstruction of light, for example by using art-recognized means and devices such as through-beam sensors.

As mentioned above, in some embodiments more than one pipette sheath aperture pair 180 is present within the sheath, as shown e.g., in FIGS. 1B and 1E. When multiple cored holes 180 are present within the pipette sheath (e.g., 2, 3, 4, 5, 6, 7, 8, 9, 10, or more), each cored hole can be present at a different position or distance along the length of pipette sheath relative to the top side of the strip 110, that defines the pipette tip aperture. By the same token, multiple sheath aperture pairs 180 can be present along the length of a single pipette sheath, wherein each sheath aperture pair 180 can be located at a different position or distance along the length of the pipette sheath 120, with respect to the top side of the strip 110, which defines the pipette tip aperture. The arrangement of a plurality of cored holes 180 along the length of the pipette sheath (whether unpaired or as part of a pipette sheath aperture pair) offers the ability to not only determine whether or not a pipette tip is present within a sheath, but further provides the capability of determining the length (size) of the pipette tip inserted within the sheath. For example, as when a shorter pipette tip is present in sheath 120, the tip may alter the reflection or the obstruction of light directed through cored hole 180a, but may be too short to alter the reflection or obstruction of light directed through cored hole 180d. By the same token, when multiple sheath aperture pairs are present, a tip present in the pipette sheath may obstruct the passage of light directed through cored hole 180a as it exits cored hole 180b, but may be too short to obstruct light passing through sheath aperture pair 180c, 180d, or 180e, 180f. The pipette sheath aperture pairs 180 thus offer advantages for quality control of the reagent strips, by enabling the rapid determination of the presence or absence of tips, which can be performed manually (e.g., visible inspection by an individual), or which can be readily automated during the manufacturing process or assembly process for the reagent strips. For example, optical sensors can be used to transmit and detect light entering or exiting the first or second cored holes of aperture pairs 180, in order to detect the presence or absence (and, e.g., length) of pipette tips within each individual sheath 120.

In addition to providing advantages for quality control, the cored holes 180 can facilitate manufacture of the reagent strips 100. Specifically, manufacture of long, relatively narrow sheaths, such as pipette sheaths 120 by injection molding poses significant challenges. The pipette sheaths typically are a long, narrow shape with low draft angle vessels. Long core pins that are conventionally used in injection molding of structures such as the pipette tip sheaths as described herein, would tend to shift under the high pressure injection of e.g., thermoplastic material or thermosetting material from which the reagent strips are made. The presence of the cored holes 180, whether present unpaired or as part of the sheath aperture pairs, enables the use of stabilizing pins, created with mold action, to be used to stabilize the long core pins that are used for the molding of the pipette sheaths 120. Accordingly, cored holes 180 make feasible the manufacture of adjoined pipette sheaths by injection molding, thereby simplifying and reducing the cost of manufacture.

In some embodiments, the reagent strip comprises pipette sheaths having the same length. In some embodiments, the reagent strip can comprise pipette sheaths having different lengths. For example, as shown in FIG. 2A, the reagent strip 100 can comprise one or more pipette sheaths 180 having a first length 230, and one or more pipette sheaths having a second length 240, as shown, for example in FIG. 2A. Thus, pipette sheaths having the first, longer length 230 can house longer pipette tips than the pipette sheaths having the second, shorter length 240. As discussed above, in some embodiments, the pipette sheaths can comprise one or more unpaired cored holes 180, or cored holes present as pipette sheath aperture pairs. In some embodiments, however, the pipette sheaths do not comprise any cored holes 180. In some embodiments, for example, a reagent strip is provided, wherein the reagent strip comprises one or more pipette sheaths having a first, longer length and having pipette sheath aperture pairs along the longer length of the sheath; and one or more pipette sheaths having a second, shorter, length and no cored holes or pipette sheath aperture pairs. In some embodiments, however, both the longer and the shorter pipette sheaths can comprise at least one unpaired cored hole 180, or at least one pipette sheath aperture pair. In some embodiments, the longer pipette sheath can comprise more unpaired cored holes 180 or pipette sheath aperture pairs than the shorter pipette sheath. By way of example, a shorter pipette sheath can contain one or two cored holes 180, or one or two pipette sheath aperture pairs, and a longer pipette sheath can contain three or four unpaired cored holes 180, or three or four pipette sheath aperture pairs.

As shown in FIG. 3, the pipette sheaths 120 are closed at their base, which provides room to collect any liquids or drippings from the pipette tips following use. The individual pipette sheaths are substantially separated, e.g., by a wall.

As discussed above, the reagent strips disclosed herein preferably comprise one or more receptacles 150. Receptacles 150 of the reagent strip can be configured to accept reagent tubes that contain, respectively, sufficient quantities of one or more reagents used to prepare and/or process the biological and/or environmental samples. In some embodiments, the reagents may be in solid form, such as in lyophilized form, for carrying out sample preparation and/or processing, e.g., isolation of nucleic acids from a sample to create a sample suitable for nucleic acid testing ("NAT") that is associated with the holder. In some embodiments, the reagents can be in liquid form.

The one or more receptacles 150 can be the same size and shape, or may be of different sizes and shapes from one another. Receptacles 150 are shown as having open bottoms, but are not limited to such topologies, and may be closed other than the inlet 220 in the upper side of the strip 110. Preferably the receptacles 150 are configured to accept commonly used containers, vessels or tubes in the field of laboratory analysis, or containers suitably configured for use with the holder herein. Reagent tubes 160 that are not integrated with strip 110 can thus be stored separately from the reagent strips, and can be snapped in just prior to use. This is advantageous as different reagents (e.g., nucleic acid extraction versus PCR reagents) may require different storage conditions. For example, lyophilized reagents can be moisture sensitive, and require different storage conditions that, e.g., a lysis buffer. The snap-in design of reagent tubes also affords versatility as tubes containing different reagents can be loaded into reagent strip 100, depending upon the different type of preparation/processing that the user wishes to perform on the sample The strips disclosed herein can include a leading edge 190. Leading edge 190 can be configured to facilitate handling by the user. Leading edge 190 can also be configured to facilitate to proper insertion and/or position of the reagent strip 100, in e.g., an automated preparation and processing device. The leading edge 190 can comprise certain identifying features, such as a color, barcode, RFID, or the like to facilitate identification and/or tracking of individual reagent strips 100.

In some embodiments, reagent strip 100 comprises a registration member such as a mechanical key 250. Typically such a key is part of the strip 110, e.g., part of the leading edge 190 or the like. A mechanical key ensures that the holder is accepted by a complementary member in, for example, a supporting rack or a receiving bay of an apparatus that controls pipetting operations on reagents in the holder. A mechanical key 250 is normally a particular-shaped cut-out that matches a corresponding cutout or protrusion in a receiving apparatus. Thus, reagent strip 100 can comprise a mechanical key 250 that comprises a pair of rectangular-shaped cut-outs on one end of the strip 110. This feature as shown additionally provides for a tab by which a user may gain a suitable purchase when inserting and removing the holder into a rack or another apparatus. The skilled artisan will appreciate that the location of the mechanical key 250 feature can be different than that shown in the figures provided herein. For example, the mechanical key 250 can be located at the other end of strip 110 than leading edge 190. In some embodiments, key 250 is an angled cutout that eases insertion of the holder into a rack, as well as ensures a good registration therein when abutting a complementary angled cut out in a recessed area configured to receive the holder. Other variations of a mechanical key are, of course, consistent with the description herein: for example, curved cutouts, or various combinations of notches or protrusions all would facilitate secure registration of the holder.

In some embodiments, the reagent strip can comprise an identifier affixed to the strip 100. The identifier may be a label, such as a writable label, a bar-code, a 2-dimensional bar-code, or an RFID tag. The identifier can be, e.g., for the purpose of quickly revealing what combination of reagents is present in the holder and, thus, for what type of sample preparation protocol it is intended. The identifier may also indicate the batch from which the holder was made, for quality control or record-keeping purposes. The identifier may also permit a user to match a particular holder with a particular sample.

As discussed above, reagent tubes 140, 160, such as containing the lyophilized reagents, can be sealed across their tops by a metal foil, such as an aluminum foil, with no plastic lining layer, as further described herein. Reagent tubes 160 containing reagents can be provided as singular tubes, or multiple tubes that comprise completely separated vessels, wherein the vessels are adjoined together, e.g., via a connector. For example, in some embodiments, more than one reagent tube 160 (e.g., two three, four, five, six, seven, eight, nine, ten, or more), can be provided together, wherein the reagent tubes are together snapped into place in adjacent receptacles 150. By way of example, a plurality of reagent tubes 160 containing reagents specific for a particular NAT assay (e.g., containing specific, lyophilized amplification primers and/or probes and/or control nucleic acids) can be adjoined together, and readily snapped into a strip 110 configured to receive the plurality of separate reagent tubes adjoined together. In other embodiments, the receptacles are configured such that reagent tubes 160 can be inserted individually into each receptacle 150.

Integral reagent tubes 140, and/or snap-in reagent tubes 160 containing different reagents may be of different colors, or color-coded for easy identification by the user. For example, color-coding integral reagent tubes 140 may be useful to distinguish different types of unitized reagent strips, e.g., that can be used in different sample preparations. In the case of the snap-in reagent tubes 160, color coding the tubes may be used to distinguish different reagents from each other. By way of example, in the case of unitized reagent strips used for DNA isolation and generating a PCR-ready sample, different color coded reagent tubes 160 can be used to distinguish tubes used in connection with different NATs, e.g., that contain different primer pairs, probes, and the like. For example they may be made of different color material, such as tinted plastic, or may have some kind of identifying tag on them, such as a color stripe or dot. They may also have a label printed on the side, and/or may have an identifier such as a barcode on the sealing layer on the top. In some embodiments, the process 130 and/or reagent tubes 140, 160 can be translucent.

The reagent strips 100 are shown configured with a waste chamber 200, having a waste inlet aperture 210 in the upper side of the strip 110. Waste chamber 200 is optional and, in embodiments where it is present, is configured to receive spent liquid reagents. In other embodiments, where it is not present, spent liquid reagents can be transferred to and disposed of at a location outside of the holder, such as, for example, a sample tube that contained the original sample whose contents are being analyzed. Waste chamber 200 is shown as part of an assembly comprising additionally two or more reagent tubes 140. It would be understood that such an arrangement is done for convenience, e.g., of manufacture; other locations of the waste chamber 200 are possible, as are embodiments in which the waste chamber 200 is adjacent a reagent tube 140, but not connected to it other than via the strip 110.

The holder is typically such that the strip 110, pipette sheath(s) 120, process tube 130, the two or more reagent tubes 140, and the waste chamber (if present) are made from a single piece, made from a material such as polypropylene. As discussed elsewhere above, the design of the embodiments disclosed herein advantageously facilitate manufacture of a unitized reagent strip from, e.g, an injection mold.

Figure 2C:
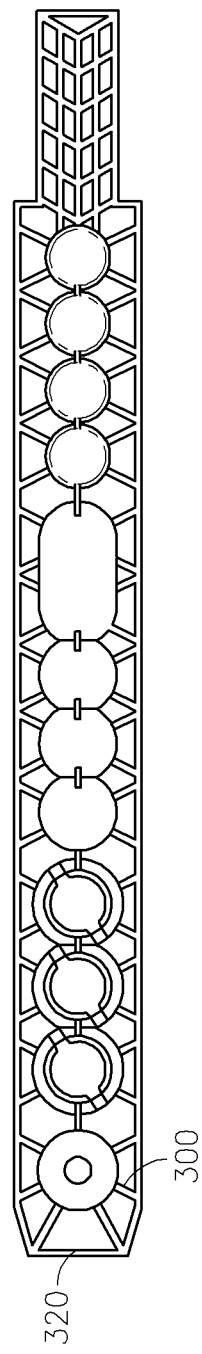

FIGS. 1G and 2C show the underside 320 of reagent strip 100. As shown in FIG. 2C, the underside 320 can comprise struts 300, which provide for stability and flexibility.

FIG. 1H shows a cut-away view of a pipette tip 360 contained in one of the pipette sheaths 120.

While the figures provided herein show a strip that is configured so that the one or more pipette sheaths, the one or more receptacles, and the respective apertures of the process tube, and the reagent tubes, are all arranged linearly with respect to one another (i.e., their midpoints lie on the same axis) the skilled artisan will appreciate that the holders herein are not limited to particular configurations of receptacles, waste chambers, process tubes, pipette sheaths, and reagent tubes. For example, some embodiments provide a shorter reagent strip e.g., with staggered apertures, wherein some reagent, process tube, or pipette tip apertures occupy 'off-axis' positions. The various receptacles, etc., also do not need to occupy the same positions with respect to one another as is shown in FIGS. 1-3, wherein the process tube is disposed approximately near the middle of the holder, liquid reagents are stored in receptacles mounted on one side of the process tube, and receptacles holding solid reagents are mounted on the other side of the process tube. Thus, in FIGS. 1-3, the process tube is on one end of the strip, and the pipette sheath(s) are at the other end, adjacent to, in an interior position, a waste chamber and two or more reagent tubes. Still other dispositions are possible, such as mounting the process tube on one end of the holder, mounting the process tube adjacent the pipette tips and pipette tip sheath (as further described herein), and mounting the waste tube adjacent the process tube. It would be understood that alternative configurations of the various parts of the reagent strip give rise only to variations of form and can be accommodated within other variations of the apparatus as described, including but not limited to alternative instruction sets for automated preparation and processing of the samples.

Process tube 130 can also be a snap-in tube, rather than being part of an integrated piece. Process tube 130 can be used for various mixing and reacting processes that occur during sample preparation. For example, cell lysis can occur in process tube 130, as can extraction of nucleic acids. Process tube 130 is then advantageously positioned in a location that minimizes, overall, pipette head moving operations involved with transferring liquids to process tube 130.

Reagent tubes 140 are typically configured to hold various liquid reagents. For example, in some embodiments, the reagent strips can comprise, three reagent tubes, wherein the individual reagent tubes are supplied with a sample wash buffer, a nucleic acid release buffer, and nucleic acid neutralization buffer, e.g., to purify nucleic acids for NAT assays.

Reagent tubes 140 that hold liquids or liquid reagents can be sealed with a laminate structure 400. The laminate structure can comprise a heat seal layer, a plastic layer such as a layer of polypropylene, and a layer of metal such as aluminum foil, wherein the heat seal layer is adjacent the one or more reagent tubes 140. The additional plastic film that is used in a laminate for receptacles that contain liquid reagents is typically to prevent liquid from contacting the aluminum.

Exemplary embodiments of a laminate structure 400, differing in their layer structures, are described, e.g., in U.S. Patent Application Publication No. 2009/0129978, herein incorporated by reference. In some embodiments, the heat seal layer of the laminate structure 400 can be made, e.g., from a lacquer or other polymer with a low melting point, and located at the top of the reagent strip 100 when so applied, as shown in FIG. 5A. The laminate 400 structure can include a plastic layer 420 on top of the heat seal layer 410 made of polypropylene, having a thickness in the range 10-50 microns. The laminate structure 400 may also include a metal layer on top of the plastic layer, comprising a layer of aluminum foil 440 bonded to the plastic layer 420 with a layer of adhesive 430. Alternatively, the metal layer may be a layer of metal that is evaporated or sputtered into place directly on to the plastic layer, as shown in FIG. 5B.

The laminates deployed herein make longer term storage easier because the holder includes the presence of sealed lyophilized reagents as well as liquids sealed in close proximity, which is normally hard to achieve.

In one embodiment, the tops of the reagent tubes have beveled edges so that when an aluminum foil is heat bonded to the top, the plastic melt does not extend beyond the rim of the tube. This is advantageous because, if the plastic melt reduces the inner diameter of the tube, it will cause interference with the pipette tip during operation. In other embodiments, a raised flat portion 260 facilitates application and removal of laminate 400. Raised surface 260, on the upper side of the connecting member, and surrounding the inlet apertures to the reagent tubes and, optionally, the waste chamber, is an optional feature of the holder.

The manner in which liquid is pipetted out is such that a pipette tip piercing through the foil rips through without creating a seal around the pipette tip. Such a seal around the tip during pipetting would be disadvantageous because a certain amount of air flow is desirable for the pipetting operation. In this instance, a seal is not created because the laminate structure 400 causes the pierced foil to stay in the position initially adopted when it is pierced. FIGS. 4A-4E illustrate the pipetting of a reagent out from a reagent tube sealed with a laminate as further described herein. At FIG. 4A, the pipette tip is positioned approximately centrally above the reagent tube 140 that contains reagent 270. At FIG. 4B, the pipette tip is lowered, usually controllably lowered, into the reagent tube, and in so doing pierces the foil 280. The exploded view of this area shows the edge of the pierced laminate to be in contact with the pipette tip at the widest portion at which it penetrates the reagent tube. At FIG. 4C, the pipette tip is withdrawn slightly, maintaining the tip within the bulk of the reagent 270. The exploded view shows that the pierced foil has retained the configuration that it adopted when it was pierced and the pipette tip descended to its deepest position within the reagent tube. At FIG. 4D, the pipette tip sucks up reagent 270, possibly altering its height. At FIG. 4E, the pipette tip is removed entirely from the reagent tube.

The materials of the various tubes and chambers may be configured to have at least an interior surface smoothness and surface coating to reduce binding of nucleic acids and other macromolecules thereto. Binding of nucleic acids is unwanted because of the reduced sensitivity that is likely to result in subsequent detection and analysis of the nucleic acids that is not trapped on the surface of the holder. The process tube also may have a low binding surface, and allows magnetic beads to slide up and down the inside wall easily without sticking to it. Moreover, it has a hydrophobic surface coating enabling low stiction of fluid and hence low binding of nucleic acids and other molecules. The reagent strips disclosed herein can be manufactured from many different polymers, including all thermoplastics, some thermosets, and elastomers. Preferably, the material is suitable for injection molding. Non limiting examples of polymers useful in the manufacture of the strips disclosed herein include, e.g., epoxy and phenolic polymers, nylon, polyethylene, and polystyrene polymers, and the like. Preferably the reagent strips are made from a plastic such as polypropylene, and are of dimensions that are rigid, so that the reagent strips will not significantly sag or flex under its own weight and will not easily deform during routine handling and transport, and thus will not permit reagents to leak out from it.

It should also be considered consistent with the description herein that a holder additionally can be configured to accept a sample, such as in a sample tube. Thus, in embodiments described elsewhere herein, a rack accepts a number of sample tubes and a number of corresponding holders in such a manner that the sample tubes and holders can be separately and independently loaded from one another. Nevertheless, in other embodiments, a holder can be configured to also accept a sample, for example in a sample tube. And thus, a complementary rack is configured to accept a number of holders, wherein each holder has a sample as well as reagents and other items. In such an embodiment, the holder is configured so that the sample is accessible to a sample identification verifier.

Kits

The reagent strips described herein may be provided as a kit. For example, individual reagent strips can be packaged together or individually in a sealed pouch, to reduce the chance of air and moisture coming into contact with the reagents in the holder. Such a sealed pouch may contain one or more of the holders described herein, such as 2, 4, 6, 8, 10, 12, 16, 20, or 24 holders.

The holder may also be provided as part of a kit for carrying out sample preparation, wherein the kit comprises a first pouch containing one or more of the holders described herein, each of the holders configured with liquid reagents for, e.g., lysis, wash, and release, and a second pouch, having an inert atmosphere inside, and one or more reagent tubes containing lyophilized PCR reagents. Such a kit may also be configured to provide for analysis of multiple samples, and contain sufficient PCR reagents (or other amplification reagents, such as for RT-PCR, transcription mediated amplification, strand displacement amplification, NASBA, helicase dependent amplification, and other familiar to one of ordinary skill in the art, and others described herein) to process such samples, and a number of individual holders such as 2, 4, 6, 8, 10, 12, 16, 20, or 24 holders.

What is claimed is:

1. A device for holding pipette tips comprising:
a strip with a top side and a bottom side;
a first pipette sheath coupled to the strip;
a second pipette sheath coupled to the strip;
a first pipette tip aperture located on the top side of the strip and configured for insertion of a first pipette tip into the first pipette sheath; and
a second pipette tip aperture located on the top side of the strip and configured for insertion of a second pipette tip into the second pipette sheath, wherein the first pipette sheath comprises an aperture pair, the aperture pair comprising a first hole and an opposing, second hole, wherein the first hole and the opposing, second hole are aligned along an axis, and wherein the first hole and the opposing, second hole are positioned along the length of the first pipette sheath.

2. The device of claim 1, further comprising a process tube coupled to the strip.

3. The device of claim 1, further comprising a reagent tube coupled to the strip.

4. The device of claim 1, wherein the first pipette sheath comprises a second aperture pair, the second aperture pair comprising a third hole and an opposing, fourth hole.

5. The device of claim 4, wherein the aperture pair is located more proximal to the strip, along the length of the first pipette sheath, than the second aperture pair.

6. The device of claim 1, wherein the first pipette sheath comprises a third hole, wherein the third hole is a different distance along the length of the first pipette sheath than the aperture pair.

7. The device of claim 1, wherein the first pipette sheath and the second pipette sheath have different lengths measured from the first pipette tip aperture and the second pipette tip aperture, respectively.

8. The device of claim 1, wherein the first pipette sheath and the second pipette sheath are integral with the strip.

9. A pipette tip holder comprising:
a strip;
a first pipette sheath, the first pipette sheath comprising a first pipette tip aperture configured to receive a first pipette tip, the first pipette sheath comprising a first longitudinal axis; and
a second pipette sheath, the second pipette sheath comprising a second pipette tip aperture configured to receive a second pipette tip, the second pipette sheath comprising a second longitudinal axis, wherein each pipette sheath is configured to surround at least a portion of the length of one pipette tip, wherein the first longitudinal axis and second longitudinal axis are spaced apart along a longitudinal axis of the strip, and wherein the first pipette sheath comprises a first hole, the first hole extending through a sidewall of the first pipette sheath.

10. The pipette tip holder of claim 9, wherein the first ole has a central axis traverse to the first longitudinal axis.

11. The pipette tip holder of claim 9, further comprising a process tube separate and spaced apart from the first pipette sheath and the second pipette sheath along the strip.

12. The pipette tip holder of claim 9, further comprising a receptacle separate and spaced apart from the first pipette sheath and the second pipette sheath along the strip, wherein the receptacle is configured to receive a reagent tube.

13. The pipette tip holder of claim 9, wherein the first pipette sheath comprises an aperture pair, the aperture pair comprising the first hole and a second hole extending through an opposing sidewall of the first pipette sheath.

14. The pipette tip holder of claim 13, wherein the first hole and the second hole are coaxial.

15. The pipette tip holder of claim 13, wherein the first hole and the second hole are positioned along the length of the first pipette sheath at the same distance from the strip.

16. The pipette tip holder of claim 9, wherein the first pipette sheath and the second pipette sheath have different lengths measured from the first pipette tip aperture and the second pipette tip aperture, respectively.

17. A method comprising:
   providing a device comprising
      a strip with a top side and a bottom side,
      a first pipette sheath configured to hold a first pipette tip, wherein the first pipette tip is configured to be inserted into the first pipette sheath via a first pipette tip aperture located in the strip, wherein the first pipette sheath comprises a first hole extending through a wall of the first pipette sheath, and
      a second pipette sheath configured to hold a second pipette tip, wherein the second pipette tip is configured to be inserted into the second pipette sheath via a second pipette tip aperture located in the strip; and
   determining whether the first pipette tip is present within the first pipette sheath by providing an optical beam that enters the first pipette sheath through the first hole.

18. The method of claim 17, wherein the determining step comprises determining the reflection or obstruction of the optical beam as indicative of the presence or absence of the first pipette tip within the first pipette sheath.

19. The method of claim 17, further comprising determining whether the first pipette tip extends within the first pipette sheath from the strip to the distance of the first hole.

20. The pipette tip holder of claim 9, wherein the first and second pipette tip apertures are spaced apart along the longitudinal axis of the strip.

* * * * *